United States Patent
Blank et al.

(10) Patent No.: US 7,519,406 B2
(45) Date of Patent: Apr. 14, 2009

(54) NONINVASIVE ANALYZER SAMPLE PROBE INTERFACE METHOD AND APPARATUS

(75) Inventors: Thomas B. Blank, Gilbert, AZ (US);
George M. Acosta, Phoenix, AZ (US);
Timothy L. Ruchti, Gilbert, AZ (US);
Mutua Mattu, Chandler, AZ (US);
Alexander D. Lorenz, Chandler, AZ (US); Kevin H. Hazen, Gilbert, AZ (US); James R. Henderson, Phoenix, AZ (US)

(73) Assignee: Sensys Medical, Inc., Chandler, AZ (US)

( * ) Notice: Subject to any disclaimer, the term of this patent is extended or adjusted under 35 U.S.C. 154(b) by 709 days.

(21) Appl. No.: 11/117,104

(22) Filed: Apr. 27, 2005

(65) Prior Publication Data
US 2005/0267342 A1 Dec. 1, 2005

Related U.S. Application Data

(60) Provisional application No. 60/605,017, filed on Aug. 27, 2004, provisional application No. 60/566,568, filed on Apr. 28, 2004.

(51) Int. Cl.
*A61B 5/1455* (2006.01)
(52) U.S. Cl. ...................... 600/310; 600/473
(58) Field of Classification Search ................. 600/310, 600/316, 322, 323, 473, 476
See application file for complete search history.

(56) References Cited

U.S. PATENT DOCUMENTS

| | | | |
|---|---|---|---|
| 4,033,054 A | 7/1977 | Fukuoka | |
| 4,213,462 A | 7/1980 | Sato | |
| 4,321,930 A | 3/1982 | Jobsis | |
| 4,548,505 A | 10/1985 | Ono | |
| 4,674,338 A | 6/1987 | Carpenter | |
| 4,798,955 A | 1/1989 | Rosenthal | |
| 4,866,644 A | 9/1989 | Shenk et al. | |
| 4,882,492 A | 11/1989 | Schlager | 250/346 |
| 5,007,423 A | 4/1991 | Branstetter et al. | |

(Continued)

FOREIGN PATENT DOCUMENTS

CN 1214768 4/1999

(Continued)

OTHER PUBLICATIONS

Webster's II New Riverside University Dictionary: The Riverside Publishing Company, 1994, p. 1000.

(Continued)

*Primary Examiner*—Eric F Winakur
(74) *Attorney, Agent, or Firm*—Michael A. Glenn; Glenn Patent Group

(57) ABSTRACT

A method and apparatus are provided for noninvasive sampling. More particularly, the method and apparatus relate to control of motion of an optical sample probe interface relative to a tissue sample site. A dynamic probe interface, is used to collect spectra of a targeted sample, control positioning of the sample probe relative to the tissue sample in terms of at least one of x-, y-, and z-axes, and/or control of sample tissue displacement to minimize spectral variations resulting from the sampling process and increase analyte property estimation precision and accuracy.

26 Claims, 18 Drawing Sheets

U.S. PATENT DOCUMENTS

| | | | |
|---|---|---|---|
| 5,068,536 A | 11/1991 | Rosenthal | |
| 5,070,874 A | 12/1991 | Barnes et al. | |
| 5,131,391 A | 7/1992 | Sakai et al. | |
| 5,170,786 A | 12/1992 | Thomas | |
| 5,285,783 A | 2/1994 | Secker | |
| 5,299,570 A | 4/1994 | Hatschek | |
| 5,348,003 A | 9/1994 | Caro | |
| 5,361,758 A | 11/1994 | Hall et al. | |
| 5,398,681 A | 3/1995 | Kupershmidt | |
| 5,448,662 A | 9/1995 | Kittell | |
| 5,492,118 A | 2/1996 | Gratton | |
| 5,506,482 A | 4/1996 | Teramatsu | |
| 5,507,288 A | 4/1996 | Bocker et al. | |
| 5,517,301 A | 5/1996 | Dave | |
| 5,548,674 A | 8/1996 | Rondeau | |
| 5,596,987 A | 1/1997 | Chance | |
| 5,619,195 A | 4/1997 | Allen | |
| 5,632,273 A | 5/1997 | Suzuki | |
| 5,636,634 A | 6/1997 | Kordis | |
| 5,655,530 A | 8/1997 | Messerschmidt | 128/633 |
| 5,661,843 A | 8/1997 | Rickenbach | |
| 5,671,317 A | 9/1997 | Veishaupt | |
| 5,687,717 A | 11/1997 | Halpern et al. | |
| 5,725,480 A | 3/1998 | Ooste | |
| 5,730,140 A | 3/1998 | Fitch | |
| 5,747,806 A | 5/1998 | Khalil et al. | 250/339.12 |
| 5,750,994 A | 5/1998 | Schlager | 250/339.11 |
| 5,769,076 A | 6/1998 | Maekawa | |
| 5,770,454 A | 6/1998 | Essenpreis et al. | |
| 5,823,951 A | 10/1998 | Messerschmidt | 600/322 |
| 5,825,488 A | 10/1998 | Kohl et al. | |
| 5,825,951 A | 10/1998 | Kitamura | |
| 5,830,132 A | 11/1998 | Robinson | |
| 5,869,075 A | 2/1999 | Krzysik | |
| 5,877,664 A | 3/1999 | Jackson, Jr. | |
| 5,879,373 A | 3/1999 | Roper et al. | |
| 5,891,021 A | 4/1999 | Dillon | |
| 5,912,656 A | 6/1999 | Tham et al. | |
| 5,935,062 A | 8/1999 | Messerschmidt et al. | 600/322 |
| 5,945,676 A | 8/1999 | Khalil et al. | 250/399.12 |
| 5,956,150 A | 9/1999 | Kanne | |
| 5,978,691 A | 11/1999 | Mills | |
| 6,014,756 A | 1/2000 | Dottling | |
| 6,040,578 A | 3/2000 | Malin et al. | 250/339.12 |
| 6,045,511 A | 4/2000 | Ott | |
| 6,067,463 A | 5/2000 | Jeng et al. | |
| 6,088,605 A | 7/2000 | Griffith et al. | |
| 6,093,156 A | 7/2000 | Cunningham et al. | |
| 6,095,974 A | 8/2000 | Shemwell et al. | |
| 6,115,673 A | 9/2000 | Malin et al. | 702/23 |
| 6,144,868 A | 11/2000 | Parker | |
| 6,152,876 A | 11/2000 | Robinson | |
| 6,157,041 A | 12/2000 | Thomas et al. | |
| 6,180,416 B1 | 1/2001 | Kuenik et al. | 436/518 |
| 6,230,034 B1 | 5/2001 | Messerschmidt et al. | 600/322 |
| 6,233,471 B1 | 5/2001 | Berner et al. | 600/345 |
| 6,236,047 B1 | 5/2001 | Malin et al. | 250/339.12 |
| 6,240,306 B1 | 5/2001 | Rohrscheib et al. | 600/316 |
| 6,272,364 B1 | 8/2001 | Kurnik | 600/345 |
| 6,280,381 B1 | 8/2001 | Malin et al. | 600/322 |
| 6,289,230 B1 | 9/2001 | Chaiken et al. | |
| 6,304,766 B1 | 10/2001 | Colvin, Jr. | 600/317 |
| 6,326,160 B1 | 12/2001 | Dunn et al. | 435/14 |
| 6,330,464 B1 | 12/2001 | Colvin, Jr. et al. | 600/316 |
| 6,334,360 B1 | 1/2002 | Chen | |
| 6,381,489 B1 | 4/2002 | Ashibe | |
| 6,400,974 B1 | 6/2002 | Lesho | 600/347 |
| 6,405,065 B1 | 6/2002 | Malin et al. | 600/310 |
| 6,411,373 B1 | 6/2002 | Garside et al. | 356/39 |
| 6,411,838 B1 | 6/2002 | Nordstrom et al. | |
| 6,415,167 B1 | 7/2002 | Blank et al. | 600/344 |
| 6,421,549 B1 | 7/2002 | Jacques | |
| 6,441,388 B1 | 8/2002 | Thomas | |
| 6,442,408 B1 | 8/2002 | Wenzel et al. | 600/310 |
| 6,449,500 B1 | 9/2002 | Asai et al. | |
| 6,456,870 B1 | 9/2002 | Rennert et al. | 600/475 |
| 6,475,800 B1 | 11/2002 | Hazen et al. | 436/8 |
| 6,487,429 B2 | 11/2002 | Hockersmith et al. | 600/316 |
| 6,493,566 B1 | 12/2002 | Ruchti et al. | 600/310 |
| 6,501,982 B1 | 12/2002 | Ruchti et al. | 600/473 |
| 6,507,687 B1 | 1/2003 | Juskaitis et al. | |
| 6,512,937 B2 | 1/2003 | Blank et al. | 600/322 |
| 6,512,982 B2 | 1/2003 | Yang et al. | |
| 6,528,809 B1 | 3/2003 | Thomas | |
| 6,546,269 B1 | 4/2003 | Kurnik | |
| 6,585,370 B2 | 7/2003 | Zelman | |
| 6,631,282 B2 | 10/2003 | Rule et al. | |
| 6,641,533 B2 | 11/2003 | Causey, III et al. | |
| 6,690,958 B1 | 2/2004 | Walker et al. | |
| 6,788,965 B2 | 9/2004 | Ruchti | |
| 6,839,583 B1 | 1/2005 | Lewandowski et al. | |
| 6,927,843 B2 | 8/2005 | Dick | |
| 7,133,710 B2 | 11/2006 | Acosta et al. | |
| 2002/0026106 A1 | 2/2002 | Khalil et al. | |
| 2003/0040663 A1 | 2/2003 | Rule | |
| 2003/0216627 A1 | 11/2003 | Lorenz | |
| 2003/0216630 A1 | 11/2003 | Jersey-Willuhn et al. | |
| 2004/0068163 A1 | 4/2004 | Ruchti | |
| 2004/0077937 A1 | 4/2004 | Yarden | |
| 2004/0127777 A1 | 7/2004 | Ruchti | |
| 2004/0163032 A1 | 8/2004 | Guo | |
| 2005/0007125 A1 | 1/2005 | Heger | |
| 2005/0267342 A1 | 12/2005 | Blank et al. | |
| 2006/0200017 A1 | 9/2006 | Monfre et al. | |

FOREIGN PATENT DOCUMENTS

| | | |
|---|---|---|
| DE | 2640987 | 3/1978 |
| EP | 1254631 | 11/2002 |
| JP | 04-215742 | 8/1992 |
| JP | 08-215180 | 8/1996 |
| JP | 2001-037741 | 2/2001 |
| JP | 2001-299727 | 10/2001 |
| JP | 2002535023 | 10/2002 |
| WO | WO96/28084 | 9/1996 |
| WO | WO97/05819 | 2/1997 |
| WO | WO 97/28437 | 8/1997 |
| WO | WO00/22982 | 4/2000 |
| WO | WO00/42907 | 7/2000 |
| WO | WO00/76575 | 12/2000 |
| WO | WO 01/31304 | 5/2001 |
| WO | WO 01/58355 | 8/2001 |

OTHER PUBLICATIONS

Diabetes Statistics. Bethesda, MD: National Institute of Health, Publication No. 98-3926, Nov. 1997.

The Diabetes Control and Complications Trial Research Group. "The effect of intensive treatment of diabetes on the development and progression of long-term complications in insulin-dependent diabetes mellitus." N Eng J of Med 1993;329:977-86.

U.K. Prospective Diabetes Study (UKPDS) Group, "Intensive blood-glucose control with sulphonylureas or insulin compared with conventional treatment and risk of complications in patients with type 2 diabetes," *Lancet*, vol. 352, pp. 837-853, 1998.

Ohkubo, Y., H. Kishikawa, E. Araki, T. Miyata, D. Isami, S. Motoyoshi, Y. Kojima, N. Furuyoshi, and M. Shichizi, "Intensive insulin therapy prevents the progression of diabetic microvascular complications in Japanese patients with non-insulin-dependent diabetes mellitus: a randomized prospective 6-year study," *Diabetes Res Clin Pract*. vol. 28, pp. 103-117, 1995.

Savitzky, A. and M. J. E. Golay. "Smoothing and Differentiation of Data by Simplified Least Squares Procedures," Anal. Chem., vol. 36, No. 8, pp. 1627-1639, 1964.

Hazen, Kevin H. "Glucose Determination in Biological Matrices Using Near-Infrared Spectr Sage, Burton H. "FDA Panel Approces Cygnus's Noninvasive GlucoWatch™", *Diabetes Technology & Therapeutics*, 2, 2000, 115-116.oscopy", doctoral dissertation, University of Iowa, 1995.

Tamada, J.A., S. Garg, L., Jovanovic, K.R. Pitzer, S. Germi, R.O. Potts, "Noninvasive Glucose Monitoring Comprehensive Clinical Results," *JAMA*, vol. 282, No. 19, pp. 1839-1844, Nov. 17, 1999.

"GlucoWatch Automatic Glucose Biographer and AutoSensors", Cygnus Inc., Document #1992-00, Rev. Mar. 2001.

Trajanowski, Zlatko; Brunner, Gernot A.; Schaupp, Lucas; Ellmerer, Martin; Wach, Paul; Pieber, Thomas R.; Kotanko, Peter; Skrabai, Falko "Open-Flow Microperfusion of Subcutaneous Adipose Tissue for ON-Line Continuous Ex Vivo Measurement of Glucose Concentration", *Diabetes Care*, 20, 1997, 1114-1120.

Trajanowski, Zlatko; Wach, Paul; Gfrerer, Robert "Portable Device for Continuous Fractionated Blood Sampling and Continuous ex vivo Blood Glucose Monitoring", *Biosensors and Bioelectronics*, 11, 1996, 479-487.

Gross, Todd M.; Bode, Bruce W.; Einhorn, Daniel; Kayne, David M.; Reed, John H.; White, Neil H.; Mastrototaro, John J. "Performance Evaluation of the MiniMed Continuous Glucose Monitoring System During Patient Home Use", *Diabetes Technology & Therapeutics*, 2, 2000, 49-56.

Rebin, Kerstin; Steil, Gary M.; Antwerp, William P. Van; Mastrototaro, John J. "Subcutaneous Glucose Predicts Plasma Glucose Independent of Insulin: Implications for Continuous Monitoring", *Am., J. Physiol.*, 277, 1999, E561-E571, 0793-1849/99, The American Physiological Society, 1999.

Geladi, P., D. McDougall and H. Martens. "Linearization and Scatter-Correction for Near-Infrared Reflectance Spectra of Meat," *Applied Spectroscopy*, vol. 39, pp. 491-500, 1985.

R. J. Barnes, M.S. Dhanoa, and S. Lister, Standard Normal Variate Transformation and De-trending of Near-Infrared Diffuse Reflectance Spectra, *Applied Spectroscopy*, 43, pp. 772-777, 1989.

T. Isaksson and B. R. Kowalski, "Piece-Wise Multiplicative Scatter Correction Applied to Near-Infrared Diffuse Transmittance Data From Meat Products", *Applied Spectroscopy*, 47, pp. 702-709, 1993.

H. Martens and E. Stark, "Extended multiplicative signal correction and spectral interference subtraction: new preprocessing methods for near infrared spectroscopy", *J. Pharm Biomed Anal*, 9, pp. 625-635, 1991.

T. Isaksson, Z. Wang, and B. R. Kowalski, Optimised scaling (OS-2) regression applied to near infrared . . . food products, *J. Near Infrared Spectroscopy*, 1, pp. 85-97, 1993.

Sum, S.T., "Spectral Signal Correction for Multivariate Calibration," Doctoral Disseration, University of Delaware, Summer 1998.

Sum, S.T. and S.D. Brown, "Standardization of Fiber-Optic Probes for Near-Infrared Multivariate Calibrations," *Applied Spectroscopy*, vol. 52, No. 6, pp. 869-877, 1998.

T. B. Blank, S.T. Sum, S.D. Brown and S.L. Monfre, "Transfer of near-infrared multivariate calibrations without standards," *Analytical Chemistry*, 68, pp. 2987-2995, 1996.

Massart, D.L., B.G.M. Vandeginste, S.N. Deming, Y. Michotte and L. Kaufman, *Chemometrics: a textbook*, New York: Elsevier Science Publishing Company, Inc., 1990.

Oppenheim, Alan V. and R. W. Schafer, *Digital Signal Processing*, Englewood Cliffs, NJ: Prentice Hall, 1975, pp. 195-271.

Otto, M., Statistics and Computer Application in Analytical Chemistry; *Chemometrics*, Weinheim: Wiley-VCH, 1999.

Beebe, K.R., R.J. Pell and M.B. Seasholtz, *Chemometrics A Practical Guide*, New York: John Wiley & Sons, Inc., 1998.

M.A. Sharaf, D.L. Illman and B.R. Kowalski, *Chemometrics*, New York: John Wiley & Sons, Inc., 1996.

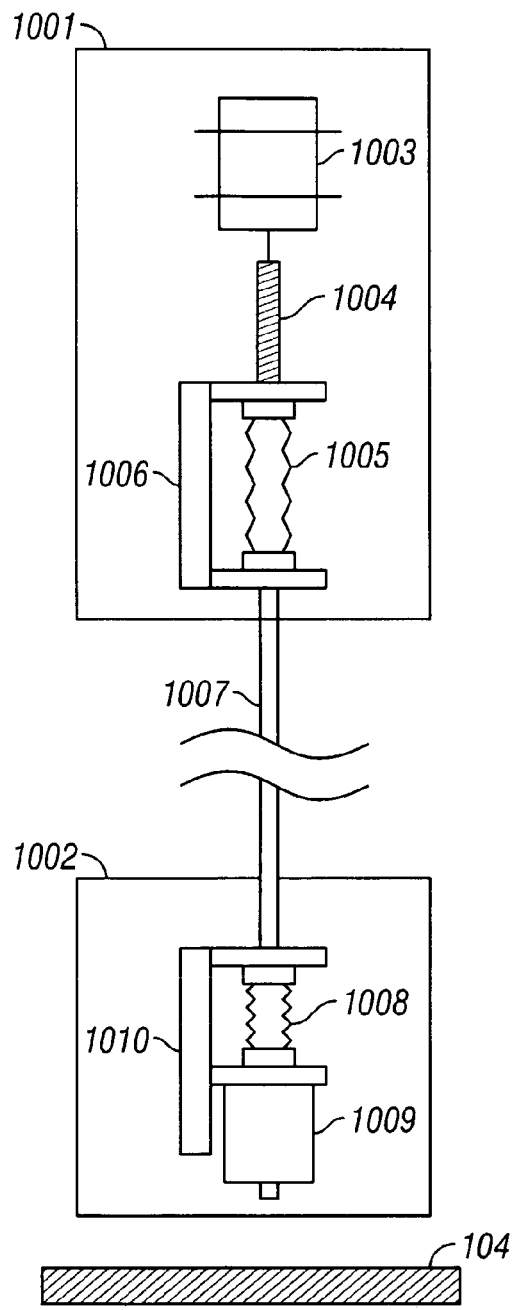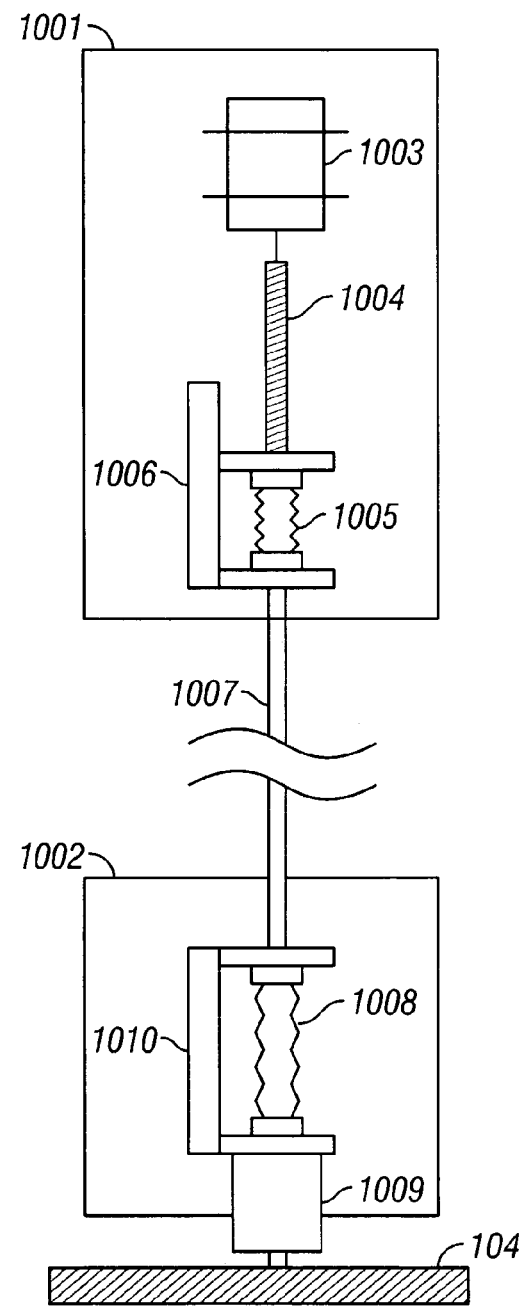
FIG. 10A            FIG. 10B

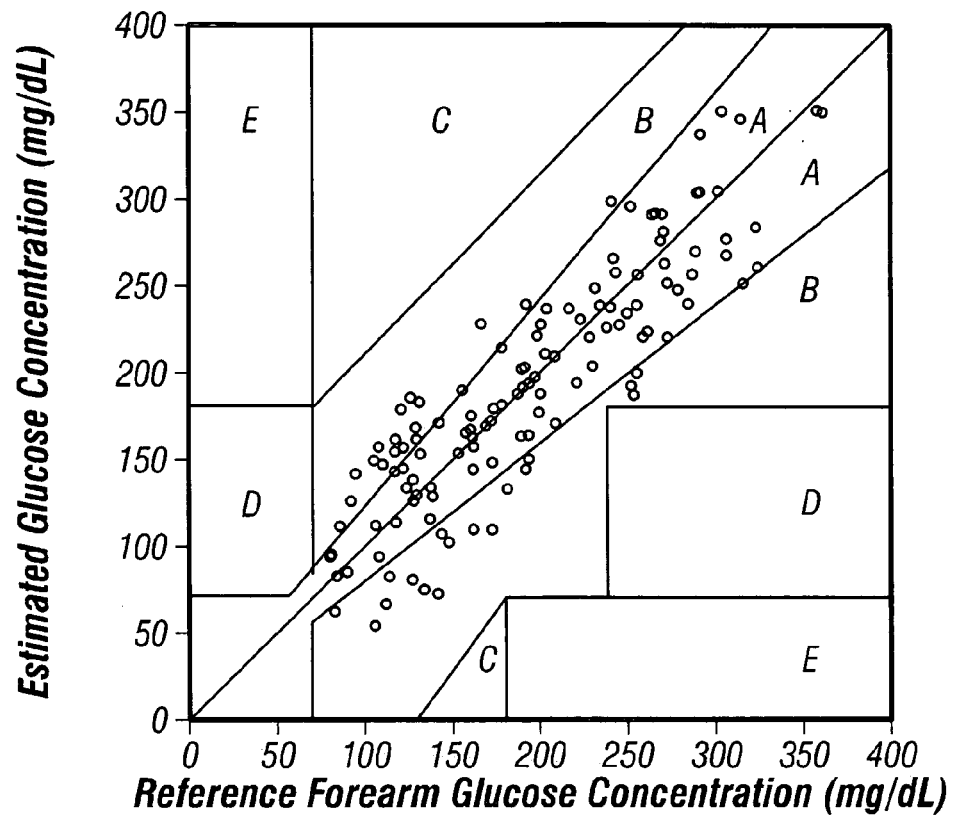
FIG. 19
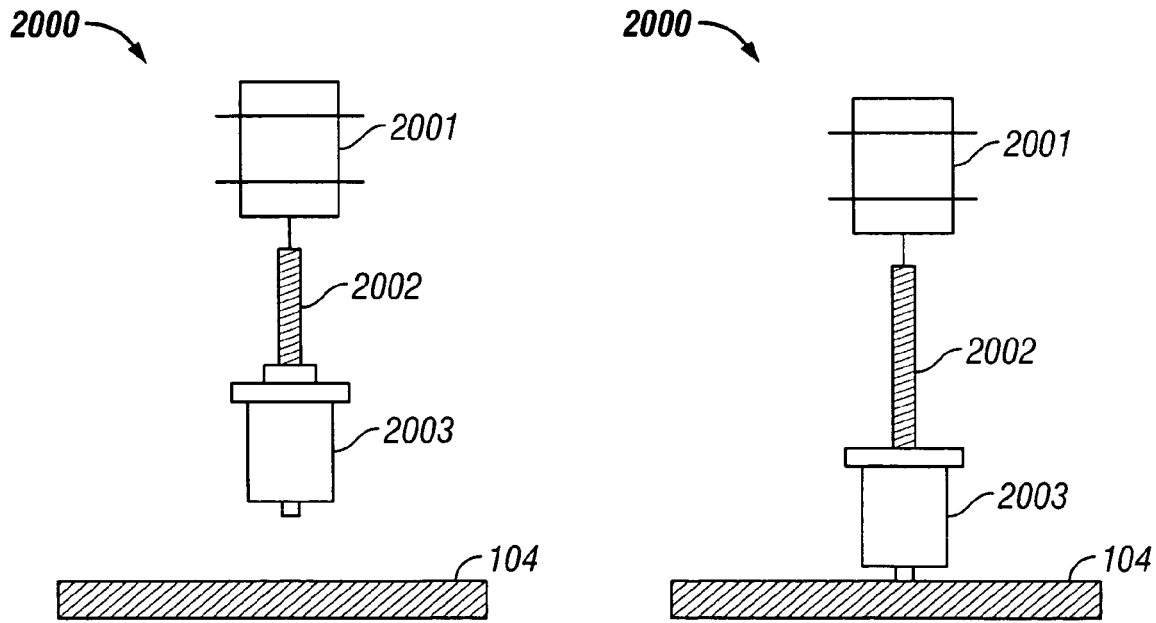
FIG. 20A
FIG. 20B

NONINVASIVE ANALYZER SAMPLE PROBE INTERFACE METHOD AND APPARATUS

CROSS REFERENCES TO RELATED APPLICATIONS

This Application:
- claims benefit of U.S. provisional patent application No. 60/605,017 filed Aug. 27, 2004; and
- claims benefit of U.S. provisional patent application No. 60/566,568 filed Apr. 28, 2004.

BACKGROUND OF THE INVENTION

1. Field of the Invention

The invention relates to noninvasive sampling. More particularly, the invention relates to a sample probe interface method and apparatus for use in conjunction with an optically based noninvasive analyzer. More particularly, the invention relates to a dynamic probe interface, wherein at least part of a sample probe moves in a controlled fashion relative to a tissue sample to control spectral variations resulting from the sample probe displacement of the tissue sample during a sampling process.

2. Description of Related Art

Spectroscopy based noninvasive analyzers deliver external energy in the form of light to a specific sampling site, region, or volume of the human body where the photons interact with a tissue sample, thus probing chemical and physical features. A number of incident photons are specularly reflected, diffusely reflected, scattered, or transmitted out of the body where they are detected. Based upon knowledge of the incident photons and detected photons, the chemical and/or structural basis of the sampled site is deduced. A distinct advantage of a noninvasive analyzer is the analysis of chemical and structural constituents in the body without the generation of a biohazard in a pain-free manner with limited consumables. Additionally, noninvasive analyzers allow multiple analytes or structural features to be determined at one time. Examples herein focus on noninvasive glucose concentration estimation, but the principles apply to other noninvasive measurements of other blood or tissue analyte properties.

Diabetes

Diabetes is a chronic disease that results in abnormal production and use of insulin, a hormone that facilitates glucose uptake into cells. While a precise cause of diabetes is unknown, genetic factors, environmental factors, and obesity play roles. Diabetics have increased risk in three broad categories: cardiovascular heart disease, retinopathy, and neuropathy. Diabetics often have one or more of the following complications: heart disease and stroke, high blood pressure, kidney disease, neuropathy (nerve disease and amputations), retinopathy, diabetic ketoacidosis, skin conditions, gum disease, impotence, and fetal complications. Diabetes is a leading cause of death and disability worldwide. Moreover, diabetes is merely one among a group of disorders of glucose metabolism that also includes impaired glucose tolerance and hyperinsulinemia, which is also known as hypoglycemia.

Sampling Methodology

A wide range of technologies serve to analyze the chemical make-up of the body. These techniques are broadly categorized into two groups, invasive and noninvasive. Herein, a technology that acquires any biosample from the body for analysis, beyond calibration, or if any part of the measuring apparatus penetrates through the outer layers of skin into the body, the technology is referred to as invasive. A number of noninvasive approaches for determining the glucose concentration in biosamples use spectrophotometric technologies. These techniques include: Raman and fluorescence, as well as techniques using light from the ultraviolet through the infrared [ultraviolet (200 to 400 nm), visible (400 to 700 nm), near-infrared (700 to 2500 nm or 14,286 to 4000 $cm^{-1}$), and infrared (2500 to 14,285 nm or 4000 to 700 $cm^{-1}$)].

Noninvasive Glucose Concentration Estimation

There exist a number of noninvasive approaches for glucose concentration estimation or determination in tissue or blood. These approaches vary widely but have at least two common steps. First, an apparatus is used to acquire a photometric signal from the body. Second, an algorithm is used to convert this signal into a glucose concentration estimation.

One type of noninvasive glucose concentration analyzer is a system performing glucose concentration estimations from spectra. Typically, a noninvasive apparatus uses some form of spectroscopy to acquire a signal, such as a spectrum, from the body. A particular range useful for noninvasive glucose concentration estimation in diffuse reflectance mode is in the near-infrared from approximately 1100 to 2500 nm or one or more ranges therein, see K. Hazen, *Glucose Determination in Biological Matrices Using Near-Infrared Spectroscopy*, doctoral dissertation, University of Iowa (1995). These techniques are distinct from the traditional invasive and alternative invasive techniques in that the interrogated sample is a portion of the human body in-situ, not a biological sample acquired from the human body.

Typically, one of several modes is used to collect noninvasive spectra including: transmittance, transflectance, and/or diffuse reflectance. In a transmittance-based concentration estimation, the signal collected, typically being light or a spectrum, is transmitted through a region of the body such as a fingertip. Transflected here refers to collection of the signal not at the incident point or area (diffuse reflectance), and not at the opposite side of the sample (transmittance), but rather at some point on the body between the transmitted and diffuse reflectance collection area. For example, transflected light enters the fingertip or forearm in one region and exits in another region typically 0.2 to 5 mm or more away depending on the wavelength used.

Diffuse reflectance spectra are generally generated by capturing at least some of the photons exiting the skin surface with zero to a few millimeters of radial travel from the location that the incident photons penetrate into the skin. Typically, light that is strongly absorbed by the body such as light near water absorbance maxima at 1450 or 1950 nm is collected after a small radial divergence in diffuse reflectance mode. Light that is less absorbed, such as light near water absorbance minima at 1300, 1600, or 2250 nm, is collected at greater radial distances and is referred to as either transflected light or diffusely reflected light. Light collected after bouncing off of the outermost surface of skin is referred to as specularly reflected light.

Calibration

Optical based glucose concentration analyzers require calibration. This is true for all types of glucose concentration analyzers such as traditional invasive, alternative invasive, noninvasive, and implantable analyzers. A fundamental feature of noninvasive glucose analyzers is that they are secondary in nature, that is, they do not measure blood glucose concentrations directly. Therefore, a primary method is required to calibrate these devices to measure blood glucose concentrations properly. Many methods of calibration exist.

One noninvasive technology, near-infrared spectroscopy, requires that a mathematical relationship between an in-vivo near-infrared spectrum and the actual blood glucose concentration is developed. This relationship is achieved through the collection of in-vivo near-infrared measurements with corresponding blood glucose concentrations that have been obtained directly through the use of measurement tools like a traditional invasive or alternative invasive reference device.

For spectrophotometric based analyzers, there are several univariate and multivariate methods that are used to develop the mathematical relationship between the measured signal and the actual blood glucose concentration. However, the basic equation being solved is known as the Beer-Lambert Law. This law states that the strength of an absorbance/reflectance measurement is proportional to the concentration of the analyte which is being measured, as in equation 1, $$A=\epsilon bC \quad (1)$$

where A is the absorbance/reflectance measurement at a given wavelength of light, $\epsilon$ is the molar absorptivity associated with the molecule of interest at the same given wavelength, b is the distance that the light travels, and C is the concentration of the molecule of interest.

Chemometric calibration techniques extract a glucose or glucose-related signal from acquired spectra through various methods of signal processing and calibration including one or more mathematical models. The models are developed through the process of calibration on the basis of an exemplary set of spectral measurements known as the calibration set and an associated set of reference blood glucose concentrations based upon an analysis of capillary blood or venous blood. Common multivariate approaches, requiring an exemplary reference glucose concentration for each sample spectrum in a calibration, include partial least squares (PLS) and principal component regression (PCR).

There are a number of reports of noninvasive glucose technologies. Some of these relate to general instrumentation configurations required for noninvasive glucose concentration estimation while others refer to sampling technologies. Those related to the present invention are briefly reviewed here:

General Instrumentation

R. Barnes, J. Brasch, D. Purdy, W. Lougheed, Non-invasive determination of analyte concentration in body of mammals, U.S. Pat. No. 5,379,764 (Jan. 10, 1995) describe a noninvasive glucose concentration estimation analyzer that uses data pretreatment in conjunction with a multivariate analysis to determine blood glucose concentrations.

P. Rolfe, Investigating substances in a patient's bloodstream, UK patent application Ser. No. 2,033,575 (Aug. 24, 1979) describes an apparatus for directing light into the body, detecting attenuated backscattered light, and using the collected signal to determine glucose concentrations in or near the bloodstream.

C. Dahne, D. Gross, Spectrophotometric method and apparatus for the non-invasive, U.S. Pat. No. 4,655,225 (Apr. 7, 1987) describe a method and apparatus for directing light into a patient's body, collecting transmitted or backscattered light, and determining glucose concentrations from selected near-infrared wavelength bands. Wavelengths include 1560 to 1590, 1750 to 1780, 2085 to 2115, and 2255 to 2285 nm with at least one additional reference signal from 1000 to 2700 nm.

M. Robinson, K. Ward, R. Eaton, D. Haaland, Method and apparatus for determining the similarity of a biological analyte from a model constructed from known biological fluids, U.S. Pat. No. 4,975,581 (Dec. 4, 1990) describe a method and apparatus for measuring a concentration of a biological analyte such as glucose using infrared spectroscopy in conjunction with a multivariate model. The multivariate model is constructed from a plurality of known biological fluid samples.

J. Hall, T. Cadell, Method and device for measuring concentration levels of blood constituents non-invasively, U.S. Pat. No. 5,361,758 (Nov. 8, 1994) describe a noninvasive device and method for determining analyte concentrations within a living subject using polychromatic light, a wavelength separation device, and an array detector. The apparatus uses a receptor shaped to accept a fingertip with means for blocking extraneous light.

S. Malin, G Khalil, Method and apparatus for multi-spectral analysis of organic blood analytes in noninvasive infrared spectroscopy, U.S. Pat. No. 6,040,578 (Mar. 21, 2000) describe a method and apparatus for estimation of an organic blood analyte using multi-spectral analysis in the near-infrared. A plurality of distinct nonoverlapping regions of wavelengths are incident upon a sample surface, diffusely reflected radiation is collected, and the analyte concentration is determined via chemometric techniques.

Specular Reflectance

R. Messerschmidt, D. Sting, Blocker device for eliminating specular reflectance from a diffuse reflectance spectrum, U.S. Pat. No. 4,661,706 (Apr. 28, 1987) describe a reduction of specular reflectance by a mechanical device. A blade-like device skims the specular light before it impinges on the detector. A disadvantage of this system is that it does not efficiently collect diffusely reflected light and the alignment is problematic.

R. Messerschmidt, M. Robinson, Diffuse reflectance monitoring apparatus, U.S. Pat. No. 5,636,633 (Jun. 10, 1997) describe a specular control device for diffuse reflectance spectroscopy using a group of reflecting and open sections.

R. Messerschmidt, M. Robinson, Diffuse reflectance monitoring apparatus, U.S. Pat. No. 5,935,062 (Aug. 10, 1999) and R. Messerschmidt, M.

Robinson, Diffuse reflectance monitoring apparatus, U.S. Pat. No. 6,230,034 (May 8, 2001) describe a diffuse reflectance control device that discriminates between diffusely reflected light that is reflected from selected depths. This control device additionally acts as a blocker to prevent specularly reflected light from reaching the detector.

Malin, supra describes the use of specularly reflected light in regions of high water absorbance such as 1450 and 1900 nm to mark the presence of outlier spectra wherein the specularly reflected light is not sufficiently reduced.

K. Hazen, G. Acosta, A. Abul-Haj, R. Abul-Haj, Apparatus and method for reproducibly modifying localized absorption and scattering coefficients at a tissue measurement site during optical sampling, U.S. Pat. No. 6,534,012 (Mar. 18, 2003) describe a mechanical device for applying sufficient and reproducible contact of the apparatus to the sampling medium to minimize specular reflectance. Further, the apparatus allows for reproducible applied pressure to the sampling site and reproducible temperature at the sampling site.

Temperature

K. Hazen, *Glucose Determination in Biological Matrices Using Near-Infrared Spectroscopy*, doctoral dissertation, University of Iowa (1995) describes the adverse effect of temperature on near-infrared based glucose concentration estimations. Physiological constituents have near-infrared absorbance spectra that are sensitive, in terms of magnitude and location, to localized temperature and the sensitivity impacts noninvasive glucose concentration estimation.

Coupling Fluid

A number of sources describe coupling fluids with important sampling parameters.

Index of refraction matching between the sampling apparatus and sampled medium is well known. Glycerol is a common index matching fluid for optics to skin.

R. Messerschmidt, Method for non-invasive blood analyte measurement with improved optical interface, U.S. Pat. No. 5,655,530 (Aug. 12, 1997), and R. Messerschmidt, Method for non-invasive blood analyte measurement with improved optical interface, U.S. Pat. No. 5,823,951 (Oct. 20, 1998) describe an index-matching medium for use between a sensor probe and the skin surface. The index-matching medium is a composition containing perfluorocarbons and chlorofluorocarbons.

M. Robinson, R. Messerschmidt, Method for non-invasive blood analyte measurement with improved optical interface, U.S. Pat. No. 6,152,876 (Nov. 28, 2000) and M. Rohrscheib, C. Gardner, M. Robinson, Method and apparatus for non-invasive blood analyte measurement with fluid compartment equilibration, U.S. Pat. No. 6,240,306 (May 29, 2001) describe an index-matching medium to improve the interface between the sensor probe and skin surface during spectroscopic analysis. The index-matching medium is preferably a composition containing chlorofluorocarbons with optional added perfluorocarbons.

T. Blank, G. Acosta, M. Mattu, S. Monfre, Fiber optic probe guide placement guide, U.S. Pat. No. 6,415,167 (Jul. 2, 2002) describe a coupling fluid of one or more perfluoro compounds where a quantity of the coupling fluid is placed at an interface of the optical probe and measurement site. Perfluoro compounds do not have the toxicity associated with chlorofluorocarbons.

Positioning

T. Blank, supra describes the use of a guide in conjunction with a noninvasive glucose concentration analyzer in order to increase precision of the location of the sampled tissue site resulting in increased accuracy and precision in noninvasive glucose concentration estimations.

J. Griffith, P. Cooper, T. Barker, Method and apparatus for non-invasive blood glucose sensing, U.S. Pat. No. 6,088,605 (Jul. 11, 2000) describe an analyzer with a patient forearm interface in which the forearm of the patient is moved in an incremental manner along the longitudinal axis of the patient's forearm. Spectra collected at incremental distances are averaged to take into account variations in the biological components of the skin. Between measurements rollers are used to raise the arm, move the arm relative to the apparatus and lower the arm by disengaging a solenoid causing the skin lifting mechanism to lower the arm into a new contact with the sensor head. The Griffith teachings do not suggest the use of a controlled pressure between the forearm sampling site and the sampling head. In addition, spectra are not collected during a period of relative motion between the sample and the analyzer.

Pressure

E. Chan, B. Sorg, D. Protsenko, M. O'Neil, M. Motamedi, A. Welch, *Effects of compression on soft tissue optical properties*, IEEE Journal of Selected Topics in Quantum Electronics, Vol. 2, No. 4, pp. 943-950 (1996) describe the effect of pressure on absorption and reduced scattering coefficients from 400 to 1800 nm. Most specimens show an increase in the scattering coefficient with compression.

K. Hazen, G. Acosta, A. Abul-Haj, R. Abul-Haj, Apparatus and method for reproducibly modifying localized absorption and scattering coefficients at a tissue measurement site during optical sampling, U.S. Pat. No. 6,534,012 (Mar. 18, 2003) describe in a first embodiment a noninvasive glucose concentration estimation apparatus for either varying the pressure applied to a sample site or maintaining a constant pressure on a sample site in a controlled and reproducible manner by moving a sample probe along the z-axis perpendicular to the sample site surface. In an additional described embodiment, the arm sample site platform is moved along the z-axis that is perpendicular to the plane defined by the sample surface by raising or lowering the sample holder platform relative to the analyzer probe tip. The '012 patent further teaches proper contact to be the moment specularly reflected light is about zero at the water bands at 1950 and 2500 nm.

M. Makarewicz, M. Mattu, T. Blank, G. Acosta, E. Handy, W. Hay, T. Stippick, B. Richie, Method and apparatus for minimizing spectral interference due to within and between sample variations during in-situ spectral sampling of tissue, U.S. Pat. No. 6,839,584 (Jan. 4, 2005) describe a temperature and pressure controlled sample interface. The means of pressure control are a set of supports for the sample that control the natural position of the sample probe relative to the sample.

To date, no FDA device has been approved for use by an individual or a medical professional for noninvasive glucose concentration estimation. Further, current reported versions of noninvasive glucose concentration analyzers do not consistently yield accurate estimations of glucose concentrations in patient trials. To be considered successful, the accuracy of estimated glucose concentrations needs to be better than 15 percent as compared to a blood analysis on greater than 90 percent of trial population. A key source of error in the glucose concentration estimation is related to the probe design and patient interface, as opposed to the spectrograph unit or algorithm design. A key parameter to control is the applied force, displacement, or pressure applied by the sample probe to the interrogated tissue volume or sample site. A force and/or displacement controlled sample interface is beneficial in generating reproducible sample spectra used in conjunction with a noninvasive analyzer and algorithm to create acceptable reproducibility and acceptable glucose concentration estimations.

Clearly, a need exists to control the load applied by the sample probe to the measurement site as a function of time.

SUMMARY OF THE INVENTION

The invention relates to noninvasive sampling. More particularly, the invention relates to a sample probe interface method and apparatus for use in conjunction with an optically based noninvasive analyzer. More particularly, the invention relates to a dynamic probe interface, wherein at least part of a sample probe moves in a controlled fashion relative to a tissue sample to control spectral variations resulting from the sample probe displacement of the tissue sample during a sampling process.

BRIEF DESCRIPTION OF THE DRAWINGS

FIGS. 10A and 10B present a schematic of a hydraulic system according to the invention;

FIG. 19 presents a concentration correlation plot of noninvasively estimated glucose concentrations versus reference glucose concentration overlaid onto a Clarke error plot according to the invention;

FIGS. 20A and 20B present a drive system coupled to a z-axis movable probe according to the invention;

DETAILED DESCRIPTION OF THE INVENTION

Overview

The invention provides a noninvasive analyzer sample probe (sampling probe) that applies a controlled displacement of the sample probe relative to a sample. One or more displaced elements of a sample module are controlled along a z-axis perpendicular to the x,y plane tangential to the surface of the sampled site. The z-axis control of the displaced sample probe element of the sample module provides for collection of noninvasive spectra with a given displacement or no displacement of a tissue sample and for collection of noninvasive spectra with varying applied displacement positions of the sample probe relative to the nominal plane of the sample tissue surface.

The ability to move a sample probe relative to the tissue sample as a function of time allows a dynamic tissue measurement. A dynamic tissue measurement is designed to collect time serial spectral data that contains the dynamic tissue response of the tissue sample as the sample probe is brought into contact with the tissue sample. In this measurement process spectral raster scans are optionally collected continuously or semi-continuously as the sample probe is moved into contact with the tissue sample or used to displace the tissue sample. For example, the sample probe is lowered slowly onto the targeted measurement site with or without an optical probe placement guide while the instrument acquires signal.

Sample probe movement is optionally controlled with an algorithm. In one embodiment, the algorithm uses features extracted from noninvasive spectra and control parameters to direct movement of the sample probe relative to the tissue sample. A feature is any derivative of a spectrum processed to enhance a particular quality that is beneficial to control. A feature is extracted information for purpose of control. Extraction of a feature typically reduces interference that is detrimental to probe movement control. Examples of feature extraction techniques include use of a derivative, a multivariate analyze, or the analysis of intensity spectra for chemical or physical signal.

Instrumentation

The following detailed description should be read with reference to the drawings in which similar elements in different drawings are numbered the same. The drawings, which are not necessarily to scale, depict illustrative embodiments that are not intended to limit the scope of the invention.

Figure 1:
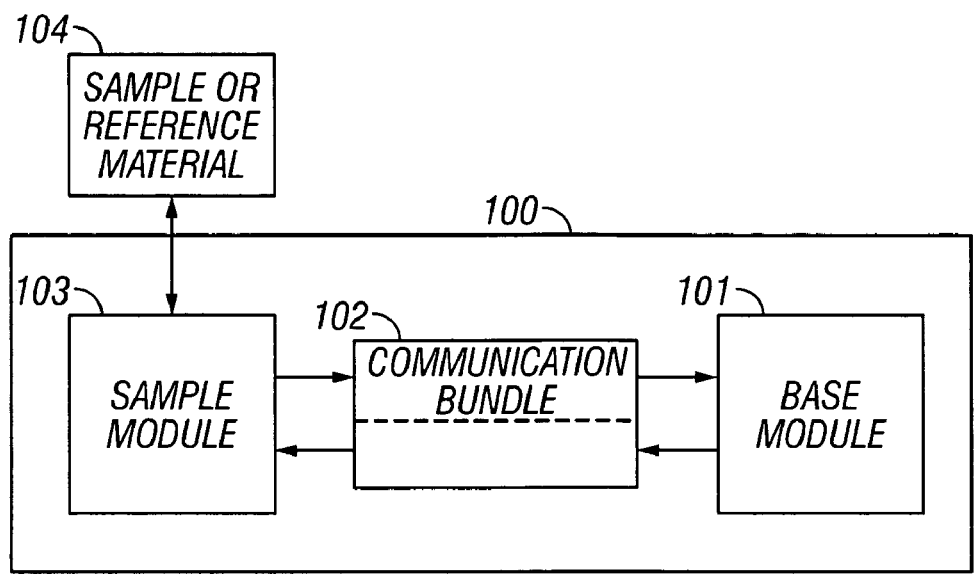
FIG. 1 provides a block diagram of a noninvasive analyzer including a base module, a communication bundle, and a sample module, wherein a sample probe position is moved along a z-axis relative to a sample according to the invention.

Referring now to FIG. 1, an analyzer is presented. An analyzer includes at least a source, a sample interface, at least one detector, and an associated algorithm. Typically, all of the components of the analyzer are included in a single unit, but need not be. In FIG. 1, an analyzer 100 is presented in terms of a base module 101, a communication bundle 102, and a sampling module 103. The sample module interfaces to a sample or reference material 104. Throughout this document, the combined base module 101, communication bundle 102, sample module 103, and algorithm is referred to as a spectrometer and/or analyzer 100.

In the case of an analyzer 100 contained in a single unit, the base module 101, communication bundle 102, and sampling module 103 are all integrated together and are contained within or integrated onto a single containing unit. Alternatively, the base module 101 is separated from the sample module 103. Communication exists between the sample module 103 and base module 101 and is presented here schematically as a communication bundle 102. In varying embodiments, the communication bundle is wireless, carries electrical power, carries data, transmits energy or movement, and/or carries fluid. For example the communication bundle 102 carries feedback control signals, temperature sensing data, coupling fluid, light, data, and/or contains hydraulic fluid.

There exist many possible configurations of analyzer elements in the base module, communication number, and sample module. In a first example, the source element is integrated into the base module and the communication bundle carries the incident optical energy to the sample. In a second example, the source element is integrated into the sample module. In both cases, photons are directed toward the tissue sample via a sample probe that is part of the sample module. In a third example, a signal collected from the sample by the sampling module is carried to the base module via the communication bundle as data or light. The base module preferably contains a detector and processing means for implementing an algorithm. The algorithm is used to process the data and/or to control collection of the data. In cases where broad band light is collected, the base module typically further includes a wavelength separation device. Additional embodiments are described in U.S. patent application Ser. No. 10/472,856 (attorney docket number SENS0011), which is herein incorporated in its entirety by this reference thereto.

Figure 2:
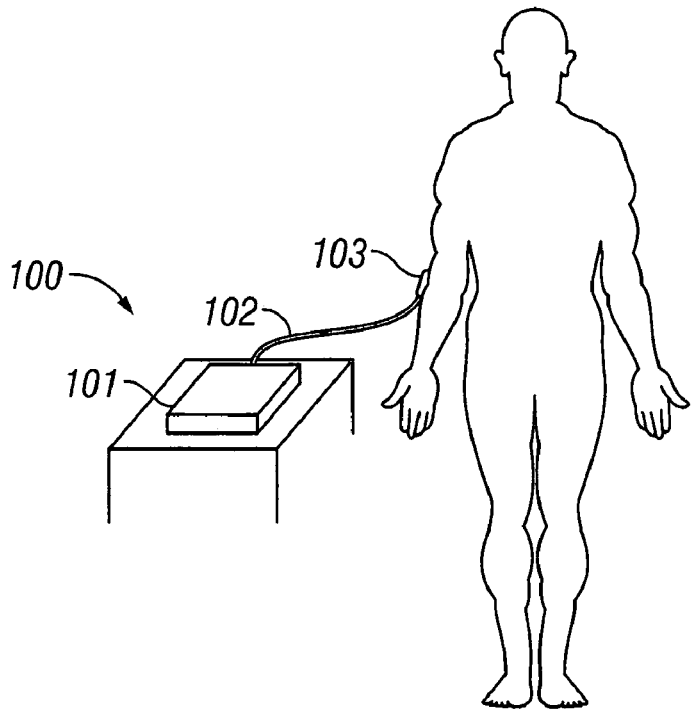
FIG. 2 presents a noninvasive analyzer including a base unit, a communication bundle, and a sample probe that is controlled by an algorithm according to the invention.

Referring now to FIG. 2, an example of a analyzer 100 with a split base module 101 and sample module 103 connected via a communication bundle 102 is presented schematically. In this example, the bulk of the analyzer is on a supporting surface, such as a tabletop or a wall or is a floor mounted unit. A smaller sample module interfaces with a sample, such as human skin tissue. This separation allows a more flexible and/or lighter sample module for use in sampling by an individual. In addition, separate housing requirements are achievable for the base module and sample module in terms of power, weight, and thermal management. In one example, a subject is sitting with their sample site, such as an arm, supported on a surface and the sample module is brought to the sample site.

Figure 3A:
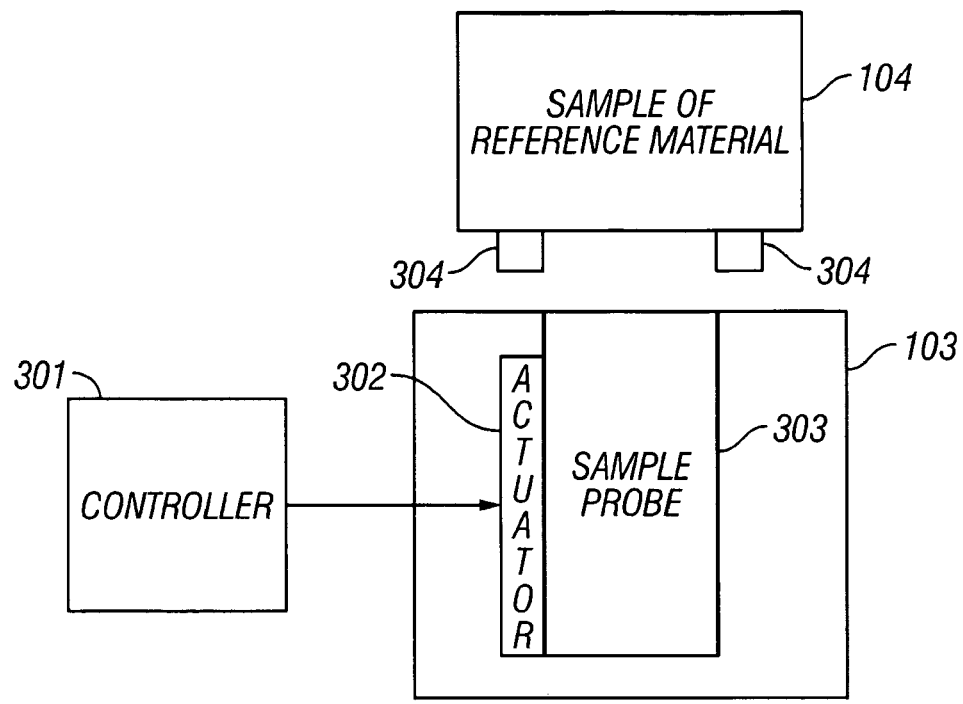
FIGS. 3A and 3B present a controller driving an actuator that moves a sample probe relative to a sample according to the invention.
Figure 3B:
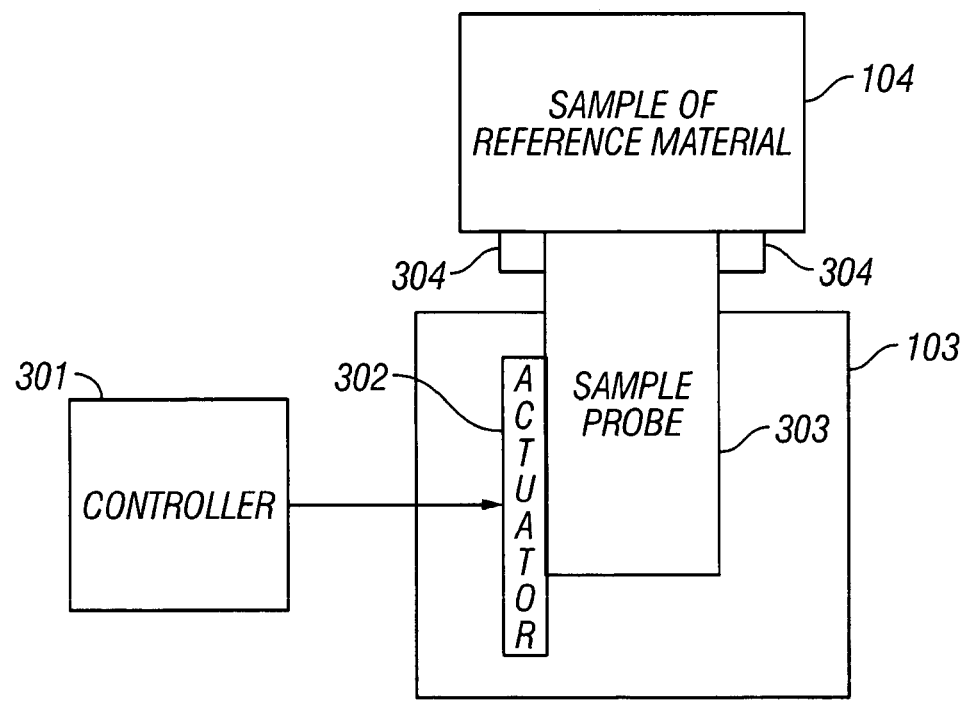

Referring now to FIGS. 3A and 3B, a schematic presentation of sample probe control and sample probe movement relative to a sample is presented. The sample module 103 includes a sample probe 303. A controller 301 controls an actuator 302 that moves the sample probe 303. Signal processing means result in a control signal that is transferred from the controller 301 to the sample probe 303 typically through an actuator 302. The communicated control signal is used to control the z-axis movement of at least part of the sample module 103 relative to the tissue sample 104 or reference material. The part of the sample module 103 movable along at least the z-axis is referred to as the sample probe or sampling probe 303. In one case, the controller sends the control signal from the algorithm to the sample module actuator, preferably via a communication bundle. In a second case, the controller 301 receives input from the sample probe or other sensor and uses the input to move the actuator 302. Thus, in various embodiments, the controller is in different locations within the analyzer, such as in the sample module 103 or in the base module 101. In these cases, the actuator 302 subsequently moves the sample probe 303 relative to the tissue sample site 104. In a third case, no controller or actuator is used and the sample probe moves in response to an outside force, such as manual operation or due to gravity. The sample probe 303 is typically controlled along the z-axis from a position of no contact, to a position of tissue sample contact, and optionally to a position of tissue sample displacement. The sample probe 303 is presented at a first (FIG. 3A) and second (FIG. 3B) instant of time with the first time presenting the sample probe when it is not in contact with the sample site. The second time presents the sample probe with minimal or nominal displacement of the sample tissue. The sample probe is, optionally, moved toward the sample, away from the sample, or remains static as a function of time as is discussed, infra. An optional guide 304 is attached to the sample and/or reference. Input to the controller 301 includes a predetermined profile, an interpretation of spectral data collected from the sample probe 303, or input from a sensor, such as a pressure sensor, an optical sensor, or a thermal sensor.

Effect of Displacement on Tissue Spectra

A study was conducted to identify effects of tissue displacement by a sample probe on noninvasive spectra. Spectra were collected with a noninvasive glucose analyzer 100 with a base module 101, a communication bundle 102, and a sampling module 103. Applicants have determined that tissue displacement by a sample probe results in corresponding variations in associated noninvasive spectra. This effect is demonstrated, infra.

Figure 4A:
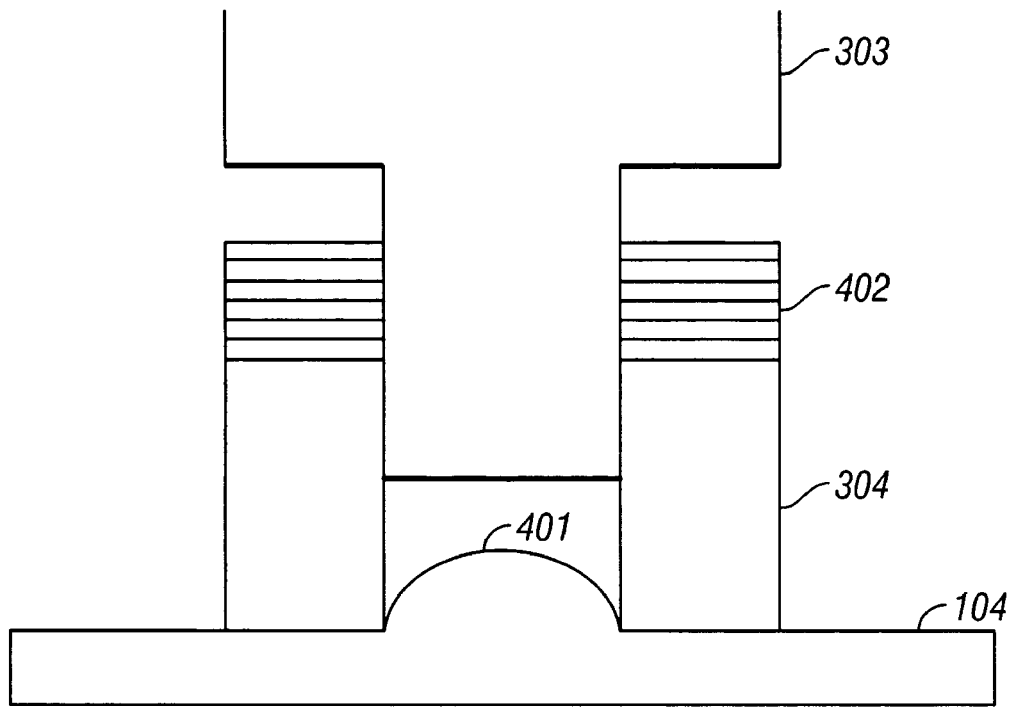
FIGS. 4A and 4B present a sample probe of the sample module positioned with (FIG. 4A) no displacement at a first period of time and (FIG. 4B) with a displacement toward a sample at a second period of time according to the invention.
Figure 4B:
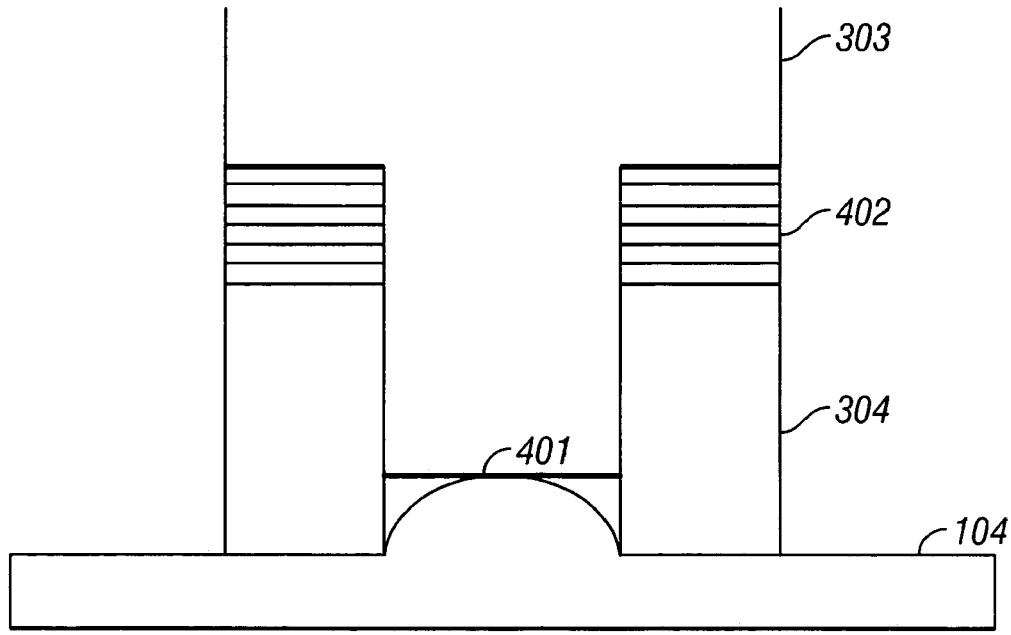

Referring now to FIGS. 4A and 4B, a movable sample probe 303 contained in a sample module 103 is presented schematically in a first position not in contact with the sample at Time 1 (FIG. 4A). In this example, the sample probe 303 is guided to the sample location with an optional guide 304 element described in T. Blank, G. Acosta, M. Mattu, S. Monfre, Fiber optic probe guide placement guide, U.S. Pat. No. 6,415,167 (Jul. 2, 2002) and U.S. patent application Ser. No. 10/170,921 filed Jun. 12, 2002, which are both herein incorporated in their entirety by this reference thereto. The guide element is replaceably attached to the sample site 104. The attachment of the guide to the sample site results in formation of a meniscus 401 of skin in the opening of the guide. The meniscus is typically a convex bulge of tissue from the nominal plane of the skin tissue but is flat or concave in some individuals, such as older individuals or individuals with less collagen density at the sample site. The size of the meniscus is subject dependent, varies on a given subject from day-to-day, and varies on a subject within a day. A series of spacers 402 placed on top of the guide provide a steric stop to the sample probe 303 as the sample probe moves down the z-axis, perpendicular to the skin surface, toward the tissue sample 104 (FIG. 4B). As individual spacers are removed, the sample probe initiates contact with the sample. Removal of additional spacers results in probe displacement of the deformable tissue sample.

Figure 5A:
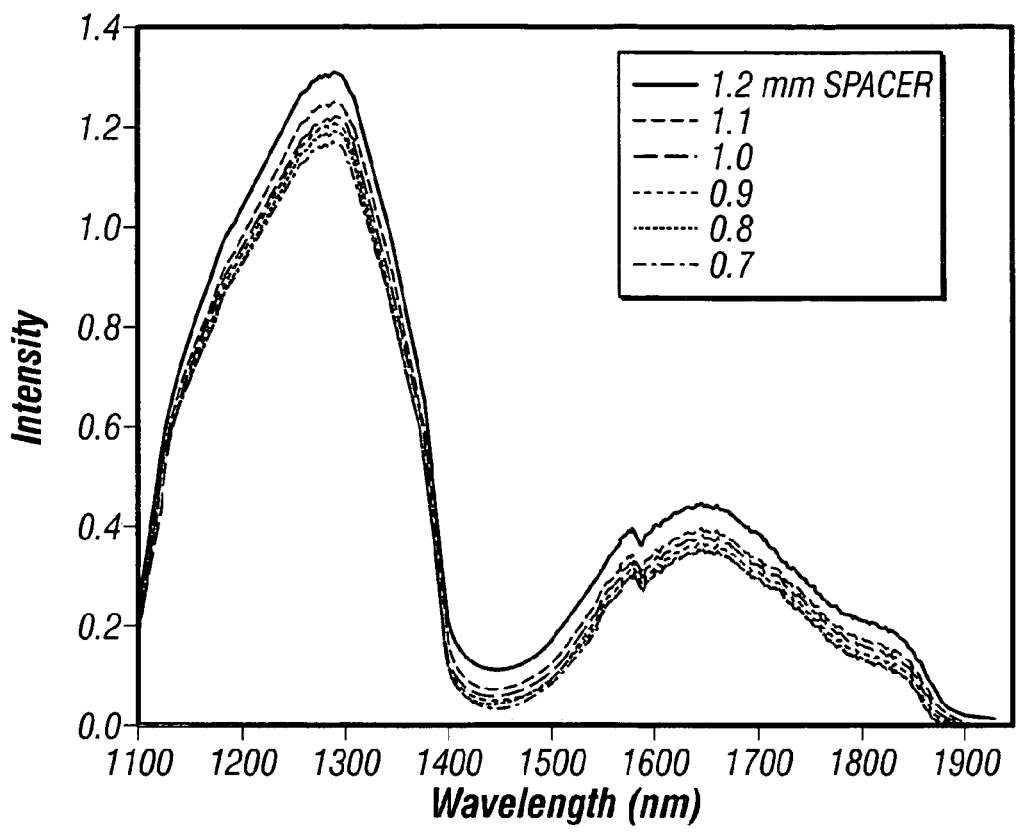
FIGS. 5A and 5B plot (FIG. 5A) noninvasive near-infrared single beam spectra collected with varying displacement of a tissue sample by a sample probe and (FIG. 5B) intensity at 1450 nm as a function of displacement according to the invention.
Figure 5B:
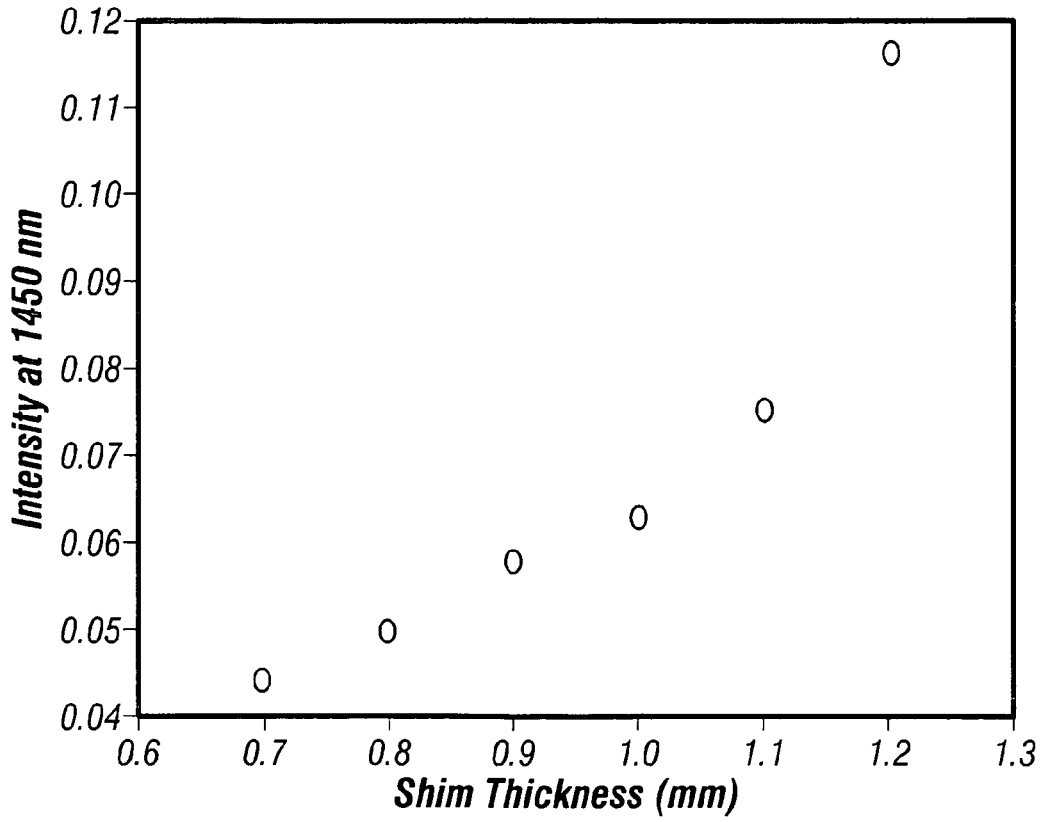

Spectra were collected with subsequent and repeated removal of a steric stop 402. The resulting single beam spectra from 1100 to 1930 nm collected with a 1.2, 1.1, 1.0, 0.9, 0.8, and 0.7 mm spacer are presented in FIG. 5A. It is the relative movement of the sample probe 303 along the z-axis relative to the tissue sample 104 that is important as opposed to the size of the spacers. The observed intensity decreases as spacers are removed and contact followed by displacement of the tissue results. Two dominant spectral features are observed: the light of the second overtone region from about 1100 to 1450 nm, and the light of the first overtone region from about 1450 to 1900 nm. The decrease in light intensity in these regions is due to chemical and physical effects including large water absorbance bands at 1450 and 1930 nm, described infra. The decrease in intensity at 1450 nm is further analyzed in FIG. 5B. The observed intensity of 0.116 volts with a 1.2 mm spacer indicates that the sample probe 303 has not yet made contact with the tissue sample 104. The large drop in observed intensity with a decrease in sample probe height of $\frac{1}{10}^{th}$ of a millimeter to 1.1 mm indicates that contact with the skin is established. This is confirmed by observing that at all wavelengths the intensity decrease is most significant with this single change in spacer height and this indicates that specularly reflected light is significantly reduced and that the resulting spectra are now dominated by the absorbance and scattering nature of the tissue sample. This pedestal effect is described in S. Malin, U.S. Pat. No. 6,040,578, supra and is incorporated herein in its entirety by this reference thereto. Subsequent removal of spacers results in a further displacement of the tissue sample by the sample probe. Increasing displacement of the tissue sample by the sample probe results in changes in the observed intensity of spectral bands associated with chemical and physical features.

Figure 6:
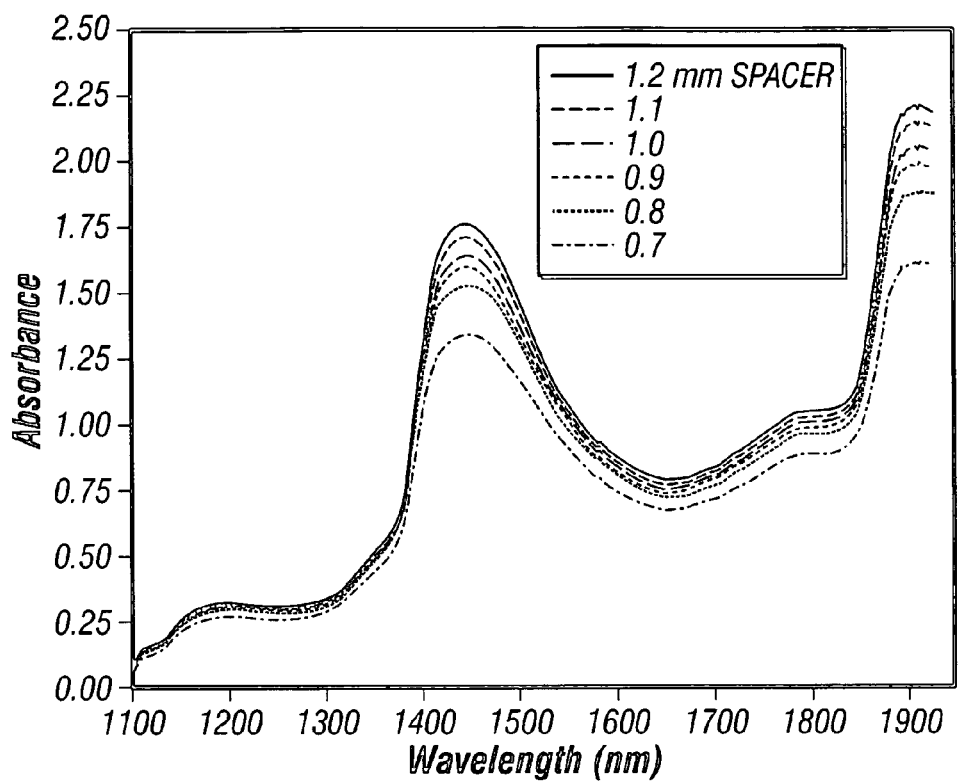
FIG. 6 presents noninvasive near-infrared absorbance spectra collected with varying displacement of the sample tissue by the sample probe according to the invention.
Figure 7:
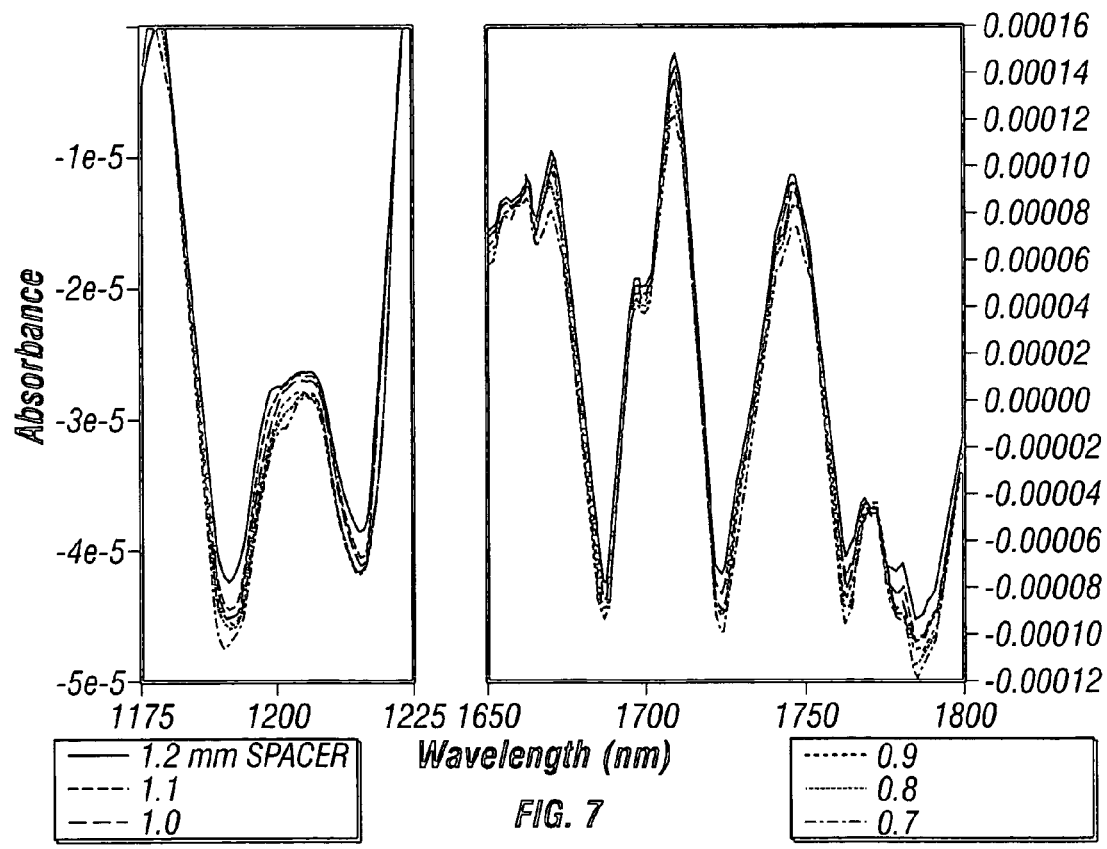
FIG. 7 plots changes in absorbance of chemical features at multiple wavelengths as a function of tissue displacement according to the invention.

Referring now to FIG. 6, the single beam spectra collected as a function of displacement of the tissue sample are subsequently converted into absorbance spectra with use of an intensity reference spectrum and are presented. The resulting absorbance spectra reveal chemical and physical features of the sample. Two large water absorbance bands are observed, one centered at about 1450 and one centered at about 1930 nm. Smaller fat and protein absorbance bands are observed in the first and second overtone spectral regions. Scattering effects are observed throughout the spectrum, but are most prevalent in the higher energy region of the spectra. In particular, larger scattering features are observed from about 1100 to 1300 nm and absorbance dominated features result from about 1300 to 1930 nm. The sample spectrum collected with a 1.2 mm radial spacer between incident and collected areas of the surface of the skin resulted in insufficient contact of the sample probe with the tissue sample and results in artificially low absorbance across the spectrum due to the collection of specularly reflected light into the collection optics of the sample probe. To enhance the chemical features observed in the first and second overtone spectral windows, the spectra were first smoothed across time and subsequently smoothed across wavelengths with a Savitsky-Golay 13-point second derivative. The resulting spectra are presented in FIG. 7. The second derivative reduces the scattering characteristics and allow the observation of the chemical features. The spectral minima observed at about 1152, 1687, and 1720 nm are dominated by the absorbance of water, protein, and fat, respectively.

Figure 8A:
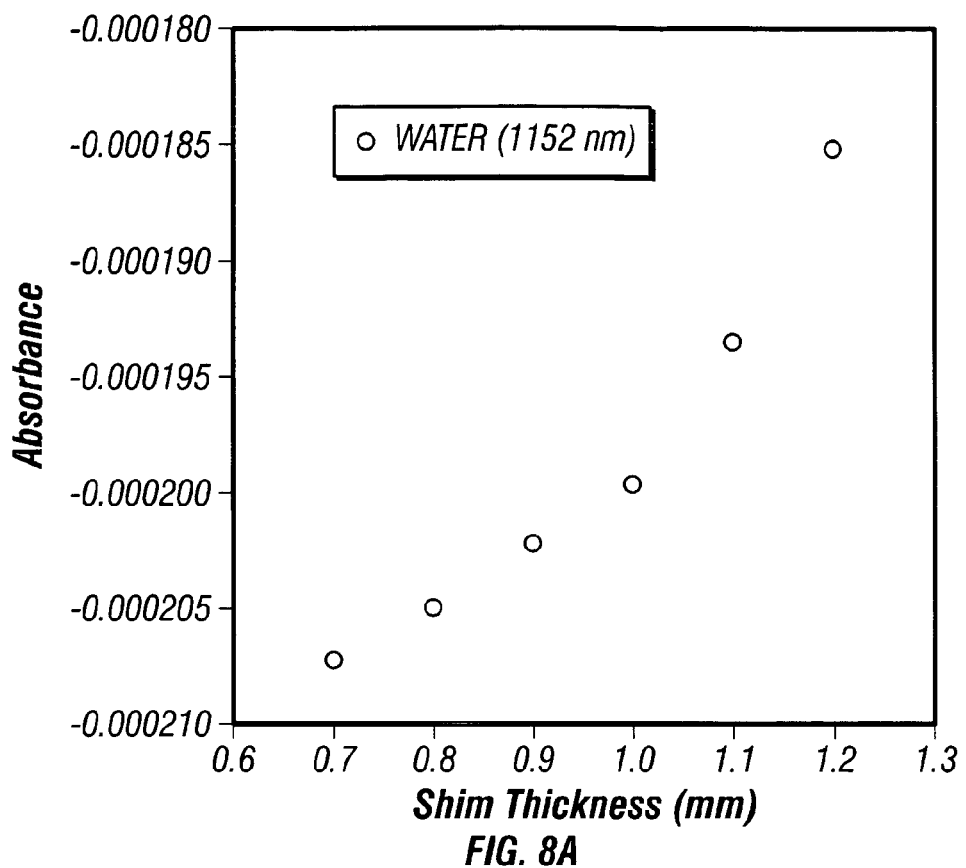
FIG. 8 plots changes in absorbance of chemical features at three wavelengths as a function of tissue displacement according to the invention.
Figure 8B:
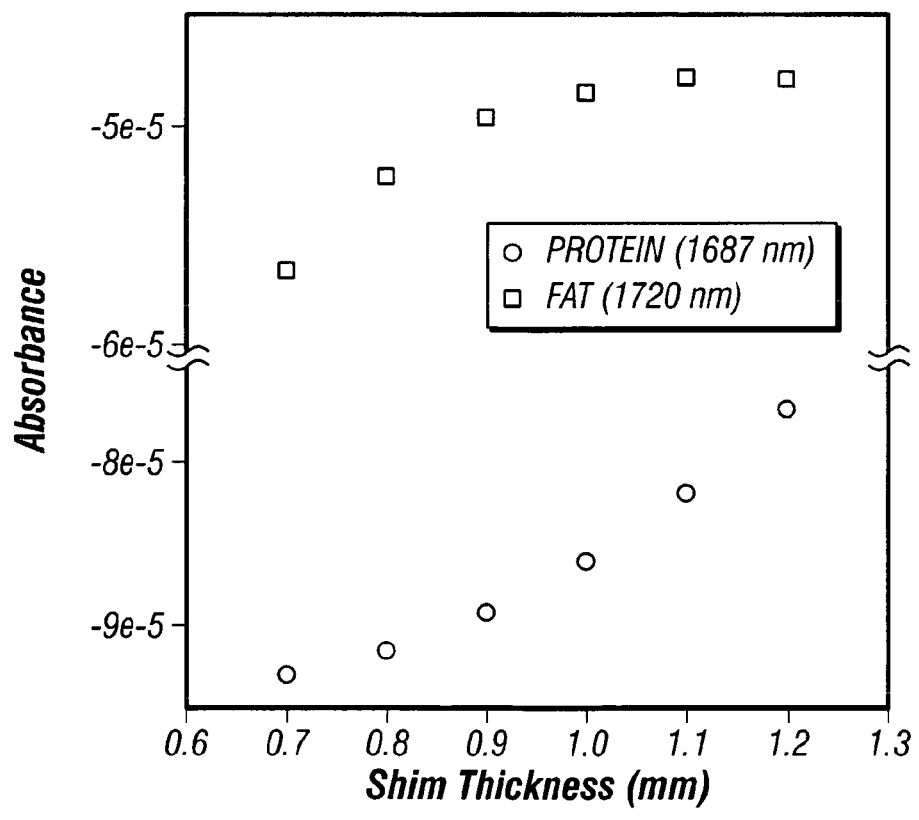

The change in absorbance of the water, protein, and fat spectral features is plotted as a function of displacement in FIG. 8. In this example, the absorbance of all three chemical features is observed to decrease with increasing displacement of the sample probe into the tissue sample. The dependence of the absorbance of the individual chemical and physical features as a function of tissue displacement is dependent upon a range of factors. The factors include:

the physical dimension of the sample probe tip interfacing with the tissue sample;
the dimension of the aperture in the guide and the chemical composition of the tissue sample;
the relative and absolute thickness of skin layers, such as the dermis;
the rate of displacement of the sample probe into the tissue; and
a hysteresis effect of previous contact of an outside object on the sample site.

The displacement of the tissue sample by the sample probe results in compression of the sample site. The displacement results in a number of changes including at least one of: a change in the localized water concentration due to fluid being displaced, a change in the localized concentration of chemicals that are not displaced such as collagen, and a correlated change in the localized scattering concentration. In addition, physical features of the sample site are changed. These changes include: compression of the epidermal ridge, compression of the dermal papilla, compression of blood capillaries, deformation of skin collagen, and/or relative movement of components embedded in skin.

Figure 9:
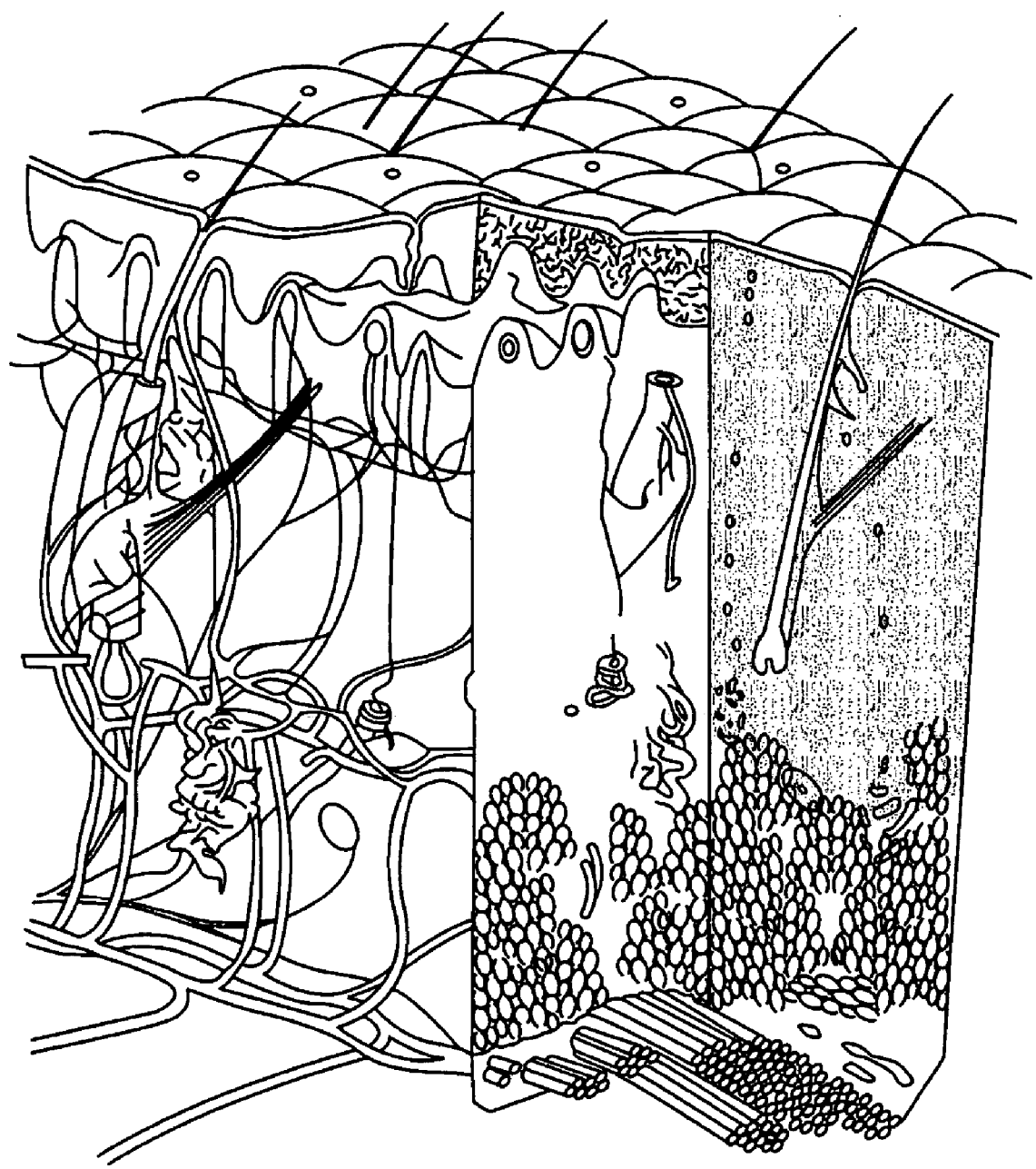
FIG. 9 shows the structure of skin.
Figure 11A:
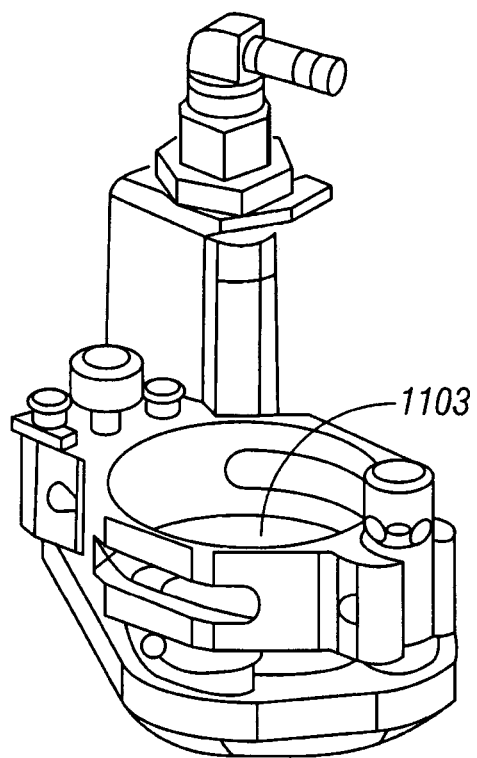
FIGS. 11A-11D present a two-dimensional rendering of an actuator system according to the invention.
Figure 11B:
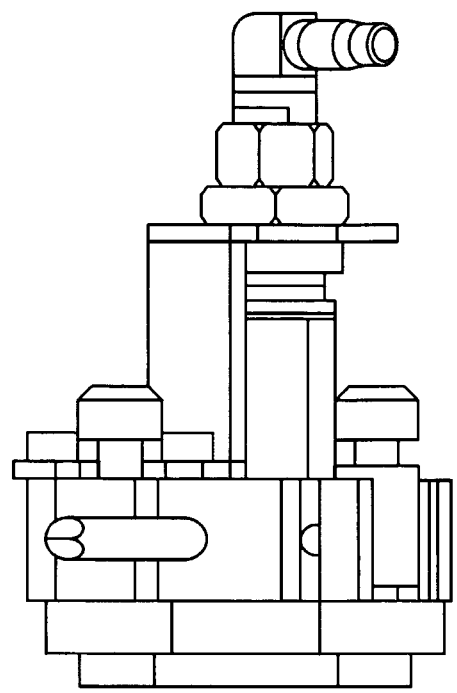
Figure 11C:
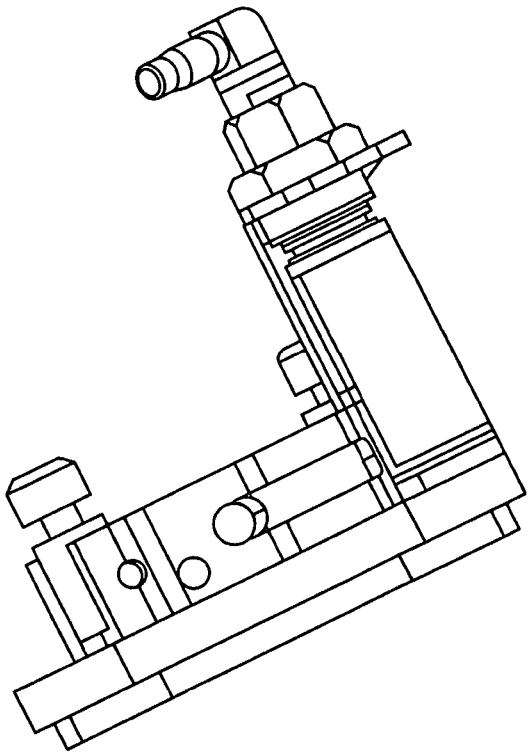
Figure 11D:
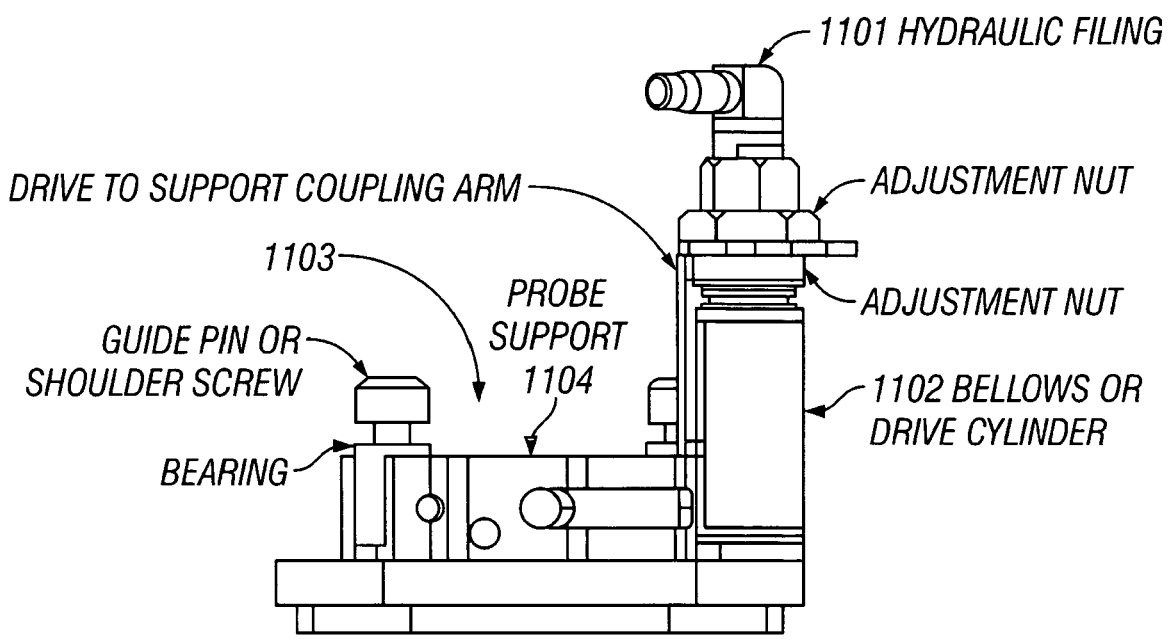

In this example, chemical and physical changes are observed with displacement of the sample probe into the tissue sample. Specific chemical features at three wavelengths are described. However, the displacement of tissue is demonstrated by this example to affect the spectra over a wide range of wavelengths from 1100 to 1930 nm. Additional spectral data show these pressure effects to be present in at least the infrared region extending out to 2500 nm. Changes in scattering are most dominant from about 1100 to 1300 nm. Further, the displacement effects described for a few particular chemical and physical structures are representative of displacement effects for a larger number of chemical and physical features. The displacement of tissue also affects a number of additional skin chemical, physical, and structural features shown in FIG. 9.

Dynamic Tissue Measurement

As discussed, supra, displacement of the tissue sample by the sample probe results in changes in noninvasive spectra. Displacement of the sample tissue is related to pressure applied to the sample tissue. However, as the tissue is deformed the return force applied by the tissue sample to the sample probe varies. Therefore, it is preferable to discuss the sample/tissue interaction in terms of displacement instead of pressure.

Response Signal

As the sample probe moves toward the sample, contacts the sample, and subsequently displaces the tissue sample, the tissue sample is deformed resulting in a number of changes including changes in scattering and absorption. Displacement and applied pressure deforms skin tissue layers resulting in changes in the optical scattering properties of the tissue sample. The change in scattering results in a transient during probe contact and a change in the pathlength of light through the tissue. Changes in the sample result in changes in the observed absorbance that are, in some cases, detrimental to noninvasive analyte concentration estimations. Absorbance changes also result from the displacement of the tissue sample by the sample probe, which causes a fluid shift from the optical measurement volume resulting in the collected photons having sampled a different optical sample. These deviations in the optical sample increase the complexity of the relationship between the spectral response and the chemical concentration.

Tissue Displacement Control

Displacement of the tissue sample by the sample probe is preferably controlled between an insufficient and excessive displacement or pressure. Insufficient contact of the sample probe with the tissue sample is detrimental. The surface of the skin tends to be rough and irregular. Insufficient contact results in a surface reflection of a portion of the incident light. Contact between the sample probe and the tissue sample minimizes air pockets and reduces optical interface reflections that contains limited useful chemical information. Optical contact needs to be sufficient to provide good optical transmission of source illumination into the capillary layer where the analytical signal exists while minimizing reflections from the surface of the skin that manifest as noise. This is aided with an optional optical fluid, such as a fluorocarbon or FC-40. Fluids used to couple light into a tissue sample are described in U.S. patent application Ser. No. 10/170,921 (attorney docket number IMET0045CIP), which is incorporated herein in its entirety by this reference thereto. Excessive displacement of the tissue sample by the sample probe is detrimental. The primary region of interest for measurement of blood borne analytes is the capillary bed of the dermis region, which is approximately 0.1 to 0.4 mm beneath the surface. The capillary bed is a compressible region and is sensitive to pressure, torque, and deformation effects. The accurate representation of blood borne analytes that are used by the body through time, such as glucose, relies on the transport of blood to and from the capillary bed, so it is not preferable to restrict this fluid movement. Therefore, contact pressure is preferably not so high as to excessively restrict or to partially restrict for an extended period of time flow of blood and interstitial fluids to the sampled tissue region.

A FIRST EXAMPLE EMBODIMENT OF THE INVENTION

In a first embodiment of the invention, the sample probe 303 is a part of the sample module 103 and the sample probe is controlled roughly along at least the z-axis, which is an axis perpendicular to the x,y plane defined by a tangential plane to the sample site.

In this first embodiment, given species types of the base module genus, sample module genus, and communication bundle genus are used. Therefore, reference numbering of the base module species, sample module species, and communication bundle species in this example are given distinct numbers from the genus.

Tissue Sample

In the first embodiment of the invention, the analyte concentration is determined using a sample site on the back of the forearm. However, other regions or volumes of the body subjected to noninvasive measurements include: a hand, finger, palmar region, base of thumb, forearm, volar aspect of the forearm, dorsal aspect of the forearm, upper arm, head, earlobe, eye, tongue, chest, torso, abdominal region, thigh, calf, foot, plantar region, and toe.

Instrumentation

In this first embodiment of the invention, hydraulics are used to move a sample probe relative to the sample along approximately the z-axis. Generally, this embodiment uses a controller to drive an actuator that, in turn, moves the sample probe. Referring now to FIGS. 10A and 10B, a specific example of an embodiment of this invention is provided schematically. A base module 1001 is connected to a sampling module 1002 via a communication bundle 1007. The base module has a drive system that moves hydraulic fluid through the communication bundle 1007. In this example, a motor 1003 is connected to a lead screw 1004 that drives a first bellows 1005. As the first bellows is compressed, hydraulic fluid is compressed through the communication bundle and the second bellows 1008 is expanded by the resultant force. As the second bellows 1008 expands, the sampling probe 1009 moves along the z-axis toward the sample 104. In this example, an optional linear bearing 1010 is used to direct the sampling probe along the z-axis. The drive system of an analyzer is shown at two points in time. At time 1 (FIG. 10A), the sampling probe is not in contact with the sample. At time 2 (FIG. 10B), the motor 1003 compresses the first bellows 1005, which expands the second bellows 1008, which in-turn advances the sampling probe 1009 into contact with the sample 104. In an optional configuration, a drive system, such as the motor 1003, is directly or indirectly attached to the sample probe 1009.

In the first embodiment presented in FIGS. 10A and 10B, a motor is used to drive a first bellows connected to a second bellows via a hydraulic line. A key aspect of this design is that the weight of the drive system is not in the sampling module that is in contact with the sample. The preferred sampling site is the dorsal aspect of the forearm. As demonstrated, supra, pressure applied to a sampled tissue volume results in changes in the spectra. It has been determined that heavy sample probe weights apply this pressure that alters the spectra. This design is exemplary of a genus of designs wherein weight of a driving system is removed from the sample module. It is also generally preferable to have the drive system be remote from the sample module in order to make the sample module smaller. However, it is recognized that it is possible to use a drive system that is in close proximity to the sample module. Alternative drive systems are presented, infra.

The inventors have discovered that even the mere weight of the sample on the sample probe leads to changes in the spectra with time. For example, if an arm sample is placed upon a sample probe, the weight of the arm on the probe results in changes in the sample site and resulting spectra as a function of time. If not accounted for, these changes detrimentally affect resultant glucose concentration estimations. Optionally a weight distribution system is used that delivers weight of a sample probe about a sample site rather than onto the sample site. For example, the physical interface of the sample probe to the sample site is around the sample site. In a first case, weight is distributed around the sample site using a flexible membrane that conforms to the shape or curvature of the sample site. In a second case, weight is distributed about the sample site using posts, a fluid filled membrane, or a set of feet. In another case, weight of the sample probe is supported by a fixture or by the base unit. In this case, the dynamic portion of the z-axis movable probe is controlled in a manner causing minimal contact or displacement of the sample probe into the sample site resulting in minimal weight, displacement, or applied pressure to the sample site.

Figure 12:
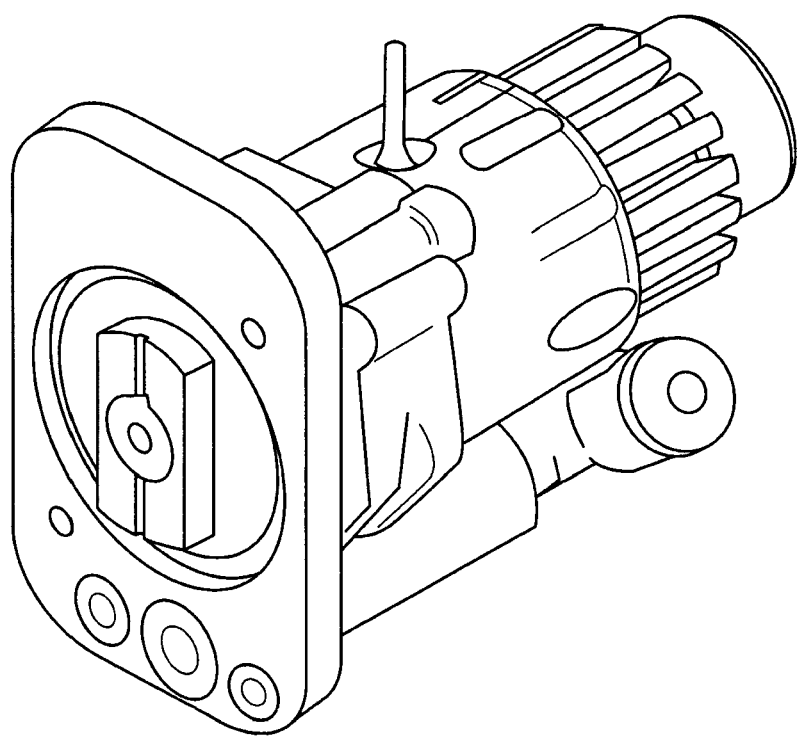
FIG. 12 presents a three-dimensional rendering of an actuator system coupled to a sample probe capable of z-axis movement according to the invention.

Referring now to FIGS. 11A-11D, a second example of a first hydraulic embodiment of the invention is presented. An actuator section of a remotely driven moving sample probe system is presented in FIGS. 11A-11D. In this example, a hydraulic line from a remote drive and control system, not shown, is the input to the hydraulic fitting 1101. The hydraulic fluid expands or compresses the bellows 1102 to move the sampling probe, not shown for clarity of presenting the actuator system. The sampling probe slides up and down the z-axis in the center of the actuator 1103. The probe is guided along the z-axis with a mechanical system, such as a probe support 1104. A three-dimensional rendering of the actuator system presented in FIGS. 11A-11D combined with the sampling probe is presented in FIG. 12. The sampling probe is moved by the actuator along the z-axis toward and/or away from a sample site.

Sampling Reproducibility

The inventors have determined that control of sampling reduces error in noninvasive analyte concentration estimation. Embodiments of the invention control parameters, such as photonic pathways, fiber stability, the sample probe/tissue sample interface, coupling fluid, thermal control, and sample probe placement, as well as the z-axis position of the sample probe relative to the x,y plane defined by the surface of the tissue sample. These parameters affect the signal-to-noise ratio of the resulting detected spectral features and are described in the following sections.

Photonic Pathways

In yet another embodiment of the invention, a sample probe with a transmissive window and a collection fiber mounted into the window is used that is approximately flush with the outermost surface of the window. The tip of the sample probe, which is moved toward and/or away from the sample, includes a single detection fiber and a transmissive window through which incident photons pass. In this example, the window dimensions are configured to allow photons to penetrate into the sample with the constraint of both a maximum and minimum radial distance to the outer dimensions of the collection fiber. The minimal distance is controlled by the buffer and sheath of the collection optics with a spacer. The maximum distance in the preferred embodiment is 1.65 mm. Alternative embodiments of the invention use a maximum radial diffusion of up to 10 mm. The inventors have determined that the number of photons propagating radially in the tissue over a distance greater than a few millimeters does not result in substantial signal so as to effectively alter the measurement.

In still yet another embodiment of the invention, a sample probe includes one or more collection fibers with a spacer about a given collection fiber that defines the minimum radial diffusion of the sample photons through the tissue sample. Spacers aid in the reduction of specularly reflected light and are used to achieve a photon profile with an average depth of penetration yielding signal to noise ratios with levels sufficient for noninvasive glucose concentration estimation. In the preferred embodiment of the invention, the maximum depth of penetration of the photons exceeds the spacer thickness. In one embodiment of the invention, a single collection fiber is used with a fiber core diameter of about 100 to 500 micrometers in diameter and preferably about 300 micrometers in diameter.

Fiber Stability

In still yet another embodiment of the invention, one or more collection fiber optics are used to direct light from the sample toward a detector. Spectral changes in the transmission characteristics of a fiber optic under various bend and flex conditions result in spectral variations, such as intensity loss, that manifest in variability in the collected spectra. A collection fiber optic runs through the communication bundle and is therefore subject to movement artifacts. Bending and movement losses from light propagating through the cladding are a large source of this variation. Light is launched into the cladding at the end of the fiber where it interfaces with the tissue sample or reference material. In addition, light is launched between the fiber cladding and core when the fiber is strained or makes a tight turn. Therefore, it is preferable to remove light traveling through the cladding by one or more mechanisms. A first mechanism is to block light entering into the fiber by reflectively coating the cladding tip of the fiber. A second mechanism provides fiber strain relief of the fiber. Strain relief is applied in at least one of several fashions. First, the fiber is loosely looped. Second, the fiber runs over a medium where it is under strain that distributes the strain of the fiber over a larger area. The fiber strain relief allows the sample probe tip to move without forcing a tight radius of curvature of the fiber thus allowing a low profile sampling module. A tight radius of curvature induces micro-cracks in the cladding that allows light to exit the core and enter the cladding where it is propagated through the communication bundle. A third mechanism applies a mode stripper to the fiber. A fourth mechanism strips the buffer material off of the cladding, preferably near the termination of the fiber. An index of refraction matching material is then coated over the fiber preferably with an index matching epoxy allowing the cladding light to bleed off of the fiber. In an example of the invention, stress relief to the fiber optic is given in the sample module by use of an exit port for the fiber running out of the sample module that has a flexible member, such as a piece of rubber, surrounding the fiber at its exit point. In addition, a mode stripper is used near the interface of the communication bundle and base module.

Sample Probe/Tissue Sample Interface

The tip of the sample probe interfaces with the tissue sample. The tissue sample does not have a perfectly flat surface. The natural curvature of the outer surface of the body yields radii of curvature ranging from approximately 1 inch (2.54 cm) for the wrist to multiple inches for the thigh or torso. In addition, the sampling module or guide is, in some instances, used to induce a tissue surface shape. For example, a guide with a center aperture induces a meniscus. The meniscus is often positive with a radius of curvature of only a few millimeters. Different sample probe tip designs accommodate these interfaces. A first option is to use a sample probe tip that matches the curvature of the body. A second option, is to deform the flexible curved surface of the tissue sample with a rigid probe tip until they conform. A third option is to use a small surface area probe tip that requires minimal conformity of the tissue sample as the tissue sample is relatively flat over a small area. A fourth option is to provide a positive curvature on the tip of the sample probe, such that the first point to contact sample tissue is the center of the sample probe tip. Example radii of curvature for the probe tip include about 1.0, 1.5, 2, 3, and 4 inches. In one example, the preferred tip of the sample probe is small, less than one square centimeter, and flat.

Coupling Fluid

In still yet another embodiment of the invention, an optional coupling fluid is used between the tip of the sample probe and the tissue sample. The coupling fluid is used for at least one of: thermal control, to minimize air at the sample probe/tissue sample interface, and to increase light coupling into and out of the skin. Precision addition of coupling fluid volumes increases the precision of resulting spectra as trapping of coupling fluid under the sample probe creates gradients of hydrostatic pressure and resultant tissue sample deformation. In addition, a uniform film thickness of coupling fluid minimizes angular distributions of the sample probe relative to the tissue sample and yields a film thickness that minimizes detection of surface specular reflections from the skin. Ranges of applied coupling fluid range from about 5 to 100 microliters with a preferable application of 20 microliters. Coupling fluid is applied to the sample site manually or in an automated fashion. An automated delivery system allows for more precise volumes to be applied, for thermal control of the coupling fluid being applied, and for ease of use by a subject. An optional auxiliary pump controlled by an algorithm is used to deliver a coupling fluid as described in U.S. patent application Ser. No. 11/031,103 (filed Jan. 6, 2005). In an automated coupling fluid delivery system, the coupling fluid is preferably delivered from a cartridge, from a reservoir in the sample module, or through a tube in the communication bundle. Optionally, the coupling fluid is thermally controlled to approximately the sample site temperature prior to delivery to the sample site in order to minimize temperature effects during sampling. In one example, about twenty microliters of a coupling fluid, such as FC-40, is applied to the sample site prior to sampling. In some embodiments, no coupling fluid is used.

In an alternative embodiment, coupling fluid between the sample probe and the tissue sample forms a small pool of about a fraction of a millimeter to 1, 2, 3, 4, or 5 mm thick. The inventors have determined that using light that is focused allows light to penetrate through the coupling fluid into the sample. This allows sampling without contact of the sample probe tip with the sample. Having an index of refraction larger than air increases the number of photons that penetrate into the skin surface.

In still another embodiment, a rounded sample probe tip, as described infra, is used in combination with a coupling fluid. Excess coupling fluid is displaced radially away from the center of the sample site as the sample probe is brought into close proximity or contact with the sample. This prevents trapped fluid from transmitting pressure from the movable sample probe to the tissue sample.

Thermal

In another embodiment, the sample probe interface is thermally controlled. Thermal control of the sample probe is important for several reasons including Food and Drug Administration (FDA) subject handling requirements, analyzer throughput stability over time, and the impact of the sample probe on the thermal characteristics of the sample interface including the sample probe tip and tissue sample.

One technique in thermal management is use of one or more optical filters to reduce the photon throughput of undesirable wavelengths to the tissue sample. The use of a filter to reduce photonic throughput results in the heating of the filter due to the conductive and/or radiative heating effects of the lamp. Preferably, the sample probe tip is thermally controlled to approximately the tissue sample surface temperature prior to contact to minimize temperature gradients at the interface that induce spectral shifts in terms of wavelength and intensity. Specific control temperatures are about 93, 94, 95, 96, 97, and 98 degrees Fahrenheit. Control of the degree of heating of the filter reduces the change in sample temperature when the sample probe is brought into contact with the tissue sample. Matching the sample probe tip temperature to the tissue sample surface temperature reduces spectral changes due to rapid heating or cooling of either the sample probe optics or the sample tissue.

Surface skin temperature is dynamic. In one embodiment of the invention, coupling fluid is thermally controlled to a target temperature. The target temperature is from 85 to 98 degrees Fahrenheit, and preferably 90±2 degrees Fahrenheit. The target temperature controlled coupling fluid is then applied to the tissue sample site. This adjusts the outer surface of the skin temperature to a known temperature. Preferably, the target temperature is slightly less than body temperature. Optionally, the tip of the sample probe is also controlled to this target temperature. Therefore, when the tip of the sample probe interfaces with the tissue sampling site, a small temperature gradient exists between the tip of the sample probe and the tissue sample site. Optionally, the reference is temperature controlled.

With a blackbody source, a filter after the source and prior to the fiber tip is preferably used to remove wavelengths that are not necessary to the measurement and that, if incident upon the skin, result in photonic heating of the tissue sample. An example is the use of silicon as described in K. Hazen, U.S. patent application Ser. No. 10/472,856, supra. The material of a sample contact optic effects the heat transfer from the sample probe tip to the tissue sample. Some optics limit the transfer of heat to the tissue such as Pyrex or fused silica with a thermal conductivity of 1.15 and 1.38 W/m-K. respectively.

These optics limit transfer of heat from the sample probe tip to the tissue sample limiting changes in the tissue sample temperature. Other materials, such as silicon with a thermal conductivity of 150 W/m-K, readily transfer heat are more conductive and rapidly bring the tissue sample surface to a set temperature. In its broadest sense, the selection of material contacting the skin is done by considering the degree to which the control of the surface of the tissue sample is to be controlled or left to its own internal thermal regulation. In one example, two filters are preferably used. The first filter removes heat originating from the source photons and the second filter limits the transfer of heat at the tissue sample site.

Sample Probe Placement

The body is a dynamic system. The sampled tissue site is also dynamic.

Through time, the sampled site changes in shape. For example, when a guide is attached to skin and/or a selected tissue sample site is repeatably tested throughout the course of a day, the formed meniscus height versus a reference position changes due to at least one of hysteresis from sampling and physiological changes of the body. Setting the sample probe tip at a fixed height then results in different displacements of the sample probe tip into the tissue sample through the period of a day resulting in different sampling. An algorithm controlled sample probe movement allows a uniform contact or a uniform displacement into the tissue sample with successive samples.

A number of algorithm approaches to controlling the sample probe movement exist including: use of specular reflectance, use of chemical information, use of physical information, use of sensor data, and pattern recognition. These approaches are discussed below.

The use of specular reflectance to control sample probe placement allows determination of contact the sample probe to the tissue sample and is taught in-part in K. Hazen, U.S. Pat. No. 6,534,012, supra, which is herein incorporated in its entirety by this reference thereto. Specular reflectance is used in a real time or post-processing outlier detection mode to determine if collected spectra or rasters are acquired when the sample probe tip is in contact with the tissue sample or to determine relative distances between the sample probe and the sample. Substantial removal of specularly reflected light, as observed in regions of high sample absorbance, indicates contact while detected signal at these wavelength regions is indicative of an air gap between the sample probe tip and the tissue sample.

Alternatively, spectra are collected or analyzed continuously or semi-continuously in a data acquisition mode. In a first case, spectra are collected according to a preset protocol. For example, a set of spectra are collected at preset intervals after initiating movement of the sample probe toward the targeted tissue site. In a second case, a real-time or semi-real time analysis is used to direct data collection based upon sensor readings. The sensor is optionally an auxiliary sensor, a contact sensor, or readings from the analyzer. For example, the analyzer collects spectra and the spectra or one or more spectral features are used to determine distance to a sample, contact, displacement, pressure, and/or specular reflectance. Examples of spectral features include an absorbance band, a scattering feature, an extracted signal, a preprocessed spectral reading, or an abstract feature. The feature is analyzed by the analyzer and is used to direct subsequent data collection. For a first example, if contact between the sample probe and sample is not obtained, then the analyzer is directed to continue moving and periodically collecting spectra. In a second example, the analyzer is told to stop moving the sample probe and to collect. In a third example, the algorithm detects specular reflectance in real time and uses this information to control an actuator that positions the sample probe tip into nominal contact with the tissue sample. Spectral acquisition is acquired at this point, after a further displacement of the sample probe tip into the tissue sample, or the sample probe is moved to a position of close proximity, such as about 0.01 to 2 mm, and spectra are again collected. This loop is repeated as needed. Generally, the signal or feature is used in an algorithm to control subsequent data collection steps.

Alternatively, in sample probe placement chemical information is used to determine contact and displacement. Chemical feature absorbances, such as water, fat, and protein are determined by the algorithm. As these features are pressure sensitive, mathematical comparisons or manipulations of the absorbances is used to determine displacement as negative, nominal, or positive.

Alternatively, in sample probe placement, physical information is used to determine negative, nominal, or positive displacement of the sample probe tip relative to the tissue sample. For example, specular reflectance is used as described, supra. Additionally, scattering information is used to determine pressure. The scattering information in the second overtone region, about 1100 to 1400 nm, is particularly useful in this regard.

In sample probe placement, sensors are also usable to determine the relative position of the sample probe tip to the tissue sample. For example, a pressure and/or temperature sensor is used to determined proximity.

Alternatively, algorithmic sample probe placement approaches such as an intelligent system or pattern recognition, are also used to control the sample probe tip location relative to the tissue sample. Typically, input to these systems is spectral and represents the chemical and physical information discussed above.

In all of these sample probe placement control algorithms, the relative position of the sample probe tip to the tissue sample is determined. An algorithm controlled movement of the sample probe from a nominal position, such as a mechanical stop or from nominal contact, is then used to control displacement into the tissue sample or to allow minimal displacement of the tissue sample by the probe tip from sample to sample. This is important as the tissue sample outer surface shape is dynamic, not consistent between individuals, and changes from sample to sample and from day to day. In one example, an algorithm is used to determine and control location of the sample probe tip relative to the sample site, as described below.

The chemical and physical features used in the above examples are exemplary. Sample probe movement is controllable with correlated information or combinations of specular, chemical, physical, and algorithm extracted features or techniques. For example, algorithm information from both chemical and scattering information is used to control the sample probe movement.

EXAMPLE DATA SET AND ANALYSIS

An example data set is collected and analyzed according to the invention using instrumentation as described herein.

Experimental

Instrumentation

A diffuse reflectance based glucose analyzer was used to collect calibration and estimation (prediction) near-infrared spectra. The glucose concentration analyzer includes a sample module and a base module coupled by a communication bundle, as described supra. The sample module includes a source, backreflector, and optics. The communication bundle carries power, hydraulic fluid, and optical signal. The base module includes a grating and a linear array detector. Wavelength and intensity references were collected and used. In this case, the wavelength reference is polystyrene and the intensity reference is polytetrafluoroethylene. The sample is a human forearm. Calibration and monitoring data were collected with both a fixed probe and a floating probe. Calibration and monitoring spectra were collected on the volar aspect of forearms and the probe had a single bundlet. Prediction spectra were collected with a z-axis movable floating probe, in a top down fiber probe configuration sampling the dorsal aspect of forearms with a single collection fiber. While the example is to specific analyzers, the invention is applicable to data matrices generated from a wide number of related analyzers and sample sites, such as those described in U.S. patent application Ser. No. 10/472,856 (attorney docket number SENS0011), which is incorporated herein in its entirety by this reference thereto.

Data Set

The analyzers in this example were used to collect a calibration, monitoring, and independent estimation (prediction) set of noninvasive spectra with correlated glucose concentrations. The calibration, monitoring, and independent estimation data set are used with the processing approach below. The calibration matrix represents 1109 spectra collected on a total of six subjects using two analyzers over an eight week period. The monitoring data set includes 1547 spectra collected on six subjects using a total of two analyzers over a period of twenty weeks. The estimation (prediction) matrix represents 126 samples from nine different subjects collected over a total of nine visits using a total of two analyzers over a period of multiple weeks.

Data Analysis

Figure 13:
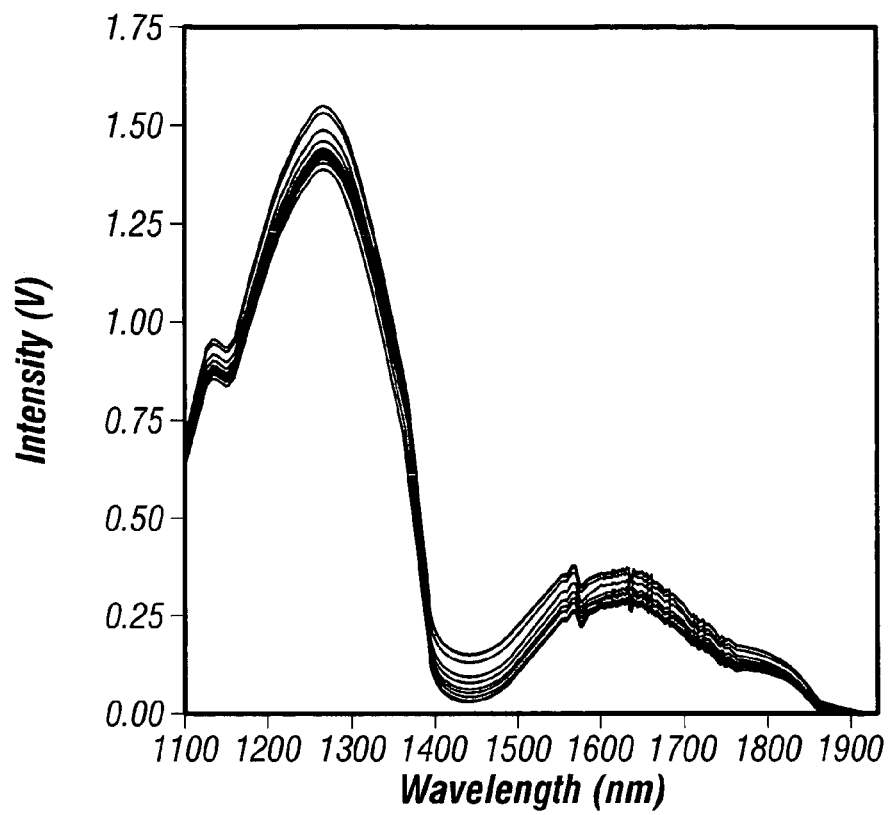
FIG. 13 presents intensity spectra collected at different z-axis positions of the sample probe relative to the sample according to the invention.

Multiple spectra, collected at varying z-axis positions of the sample probe relative to the sample, used to create a single replicate are herein referred to as rasters or raster spectra. Referring now to FIG. 13, intensity raster spectra associated with a given sample of a given subject that are used to estimate (predict) a single glucose concentration are presented. These raster spectra, which are used to generate a single glucose concentration estimation, are collected with a z-axis movement rate of 32.5 µm/second, where a spectrum is collected every 0.2 seconds while the sample probe moved toward the sample through a total throw distance of the sample probe of 0.95 mm. Every tenth spectrum collected on the first sample is presented in FIG. 13. The intensity in both the second overtone spectral region (about 1100 to 1450 nm) and first overtone spectral region (about 1450 to 1900 nm) are observed to decrease in magnitude as the sample probe approaches and makes contact with the sample. The higher intensities represent non-contact of the sample probe with the sample. Intermediate intensities represent contact of the sample probe with a fluorocarbon contact fluid, such as FC-40. The smaller intensities represent contact of the sample probe with the sample. The last intensities collected represent displacement of the sample by the sampling probe.

Figure 14:
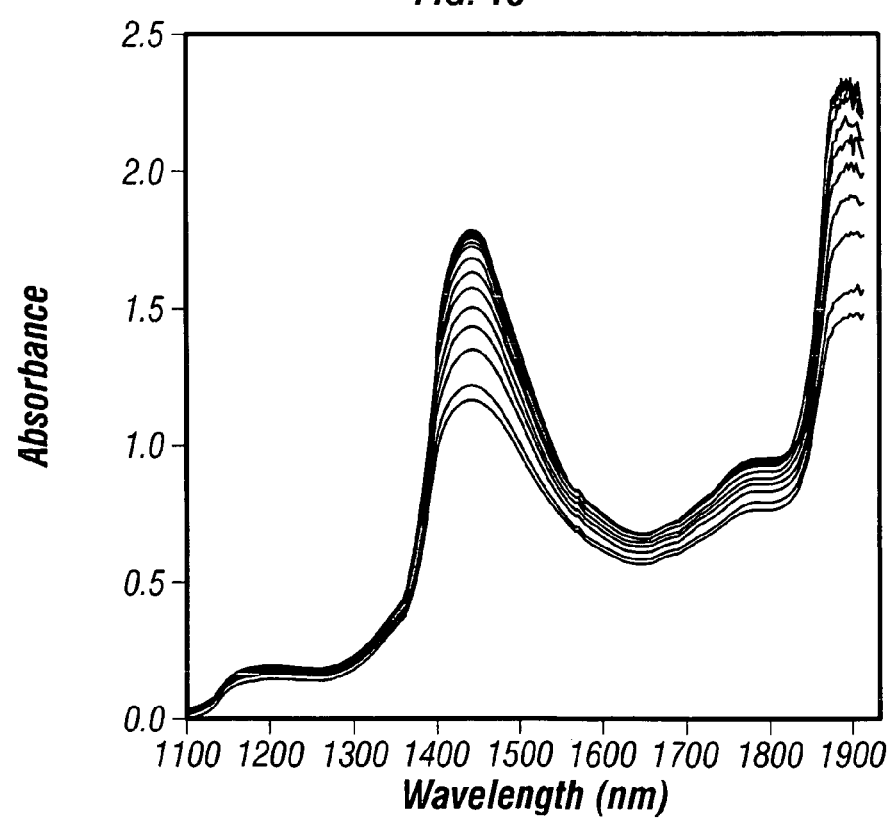
FIG. 14 presents absorbance spectra collected at different z-axis positions of the sample probe relative to the sample according to the invention.

Referring now to FIG. 14, the time based intensity spectra of the rasters of a given sample of a given subject, presented in FIG. 13, are converted to absorbance. It is observed that the absorbance decreases as the sample probe moves toward the sample. This is largely the removal of specularly reflected light. For example, the light intensity approaches zero at 1450 nm where there is a large water absorbance band as the sample probe moves toward making contact with the sample.

Figure 15:
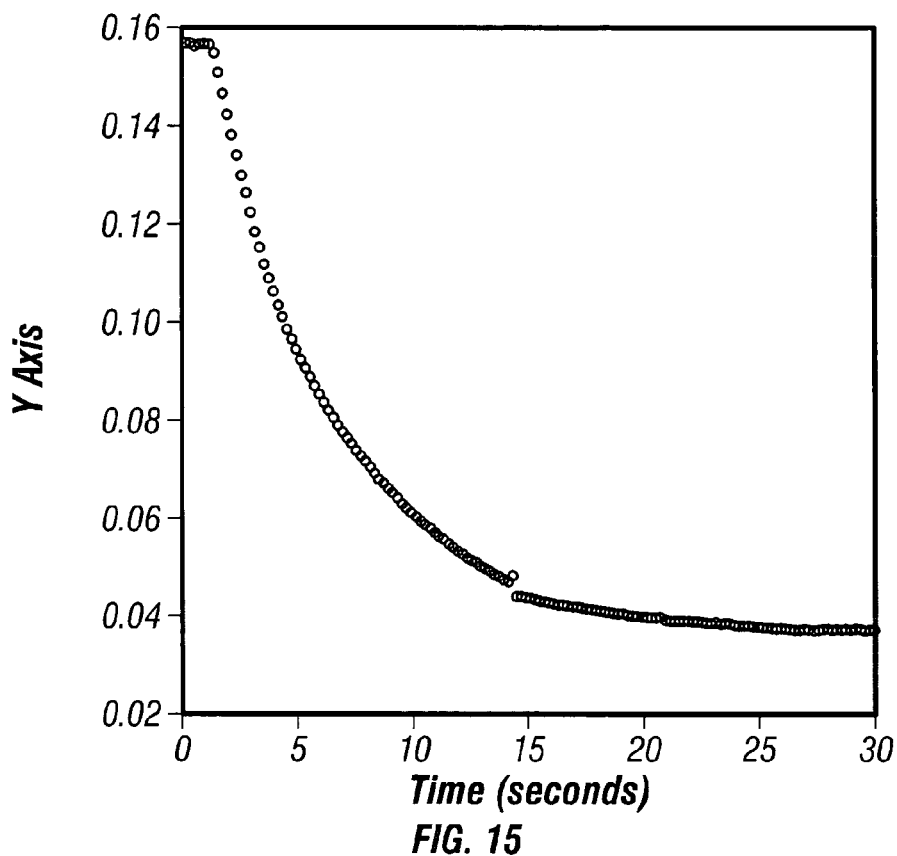
FIG. 15 presents the intensity at a water absorbance band of a given sample of a given subject as the position of the sample probe moves along the z-axis toward the sample according to the invention.

For this sample, every raster intensity reading at 1450 nm is presented in FIG. 15. The intensity is observed to drop off rapidly as the sample probe approaches the sample, to have a spike when the fluorocarbon fluid is reached or when the sampling probe makes contact with the sample, and to level off generally as the sample probe minimally displaces the sample. The spike is determined to be larger with rapid velocities of the sample probe. An increase in the observed intensity is often observed with increasing displacement of the sampling probe into the sample. This is a pressure effect that displaces water. In general, wavelengths from about 1400 nm to 1900 nm are dominated by absorbance, as opposed to scattering, and the intensity at the large water absorbance band at 1450 nm is associated with the coefficient of absorbance of the sample.

Figure 16:
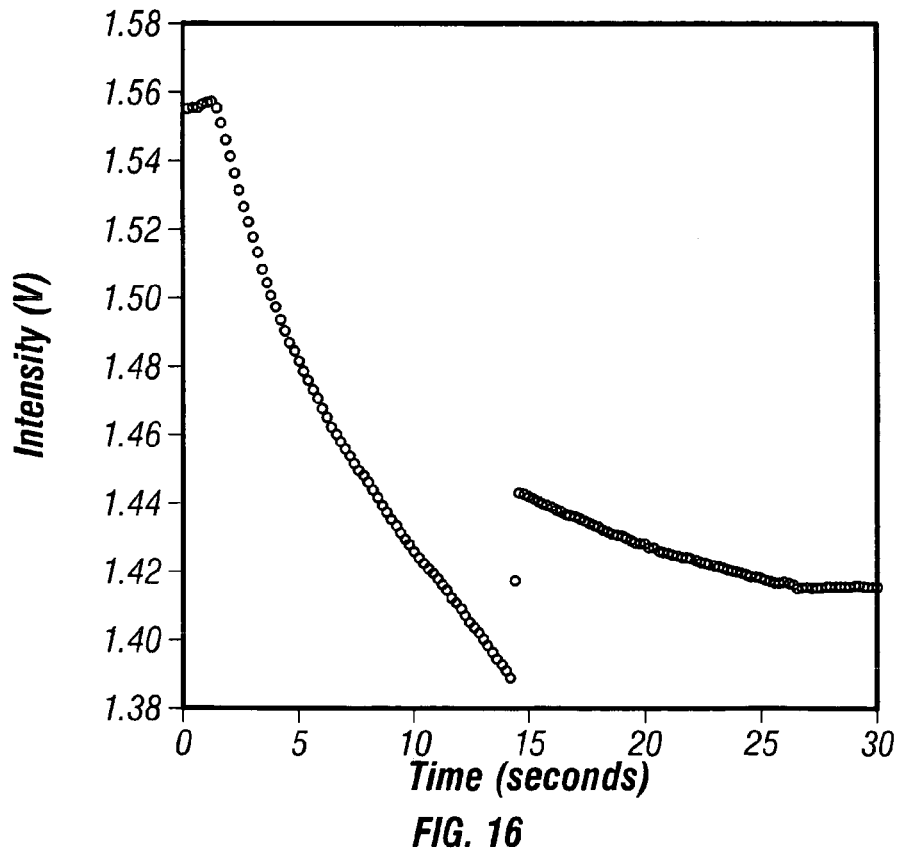
FIG. 16 presents the intensity in the second overtone region of a given sample of a given subject as the position of the sampling probe moves along the z-axis toward the sample according to the invention.

Referring now to FIG. 16, the intensity of every raster spectrum of this sample of this subject at 1271 nm is presented. In the second overtone region, the intensity reading has a large scattering parameter in combination with the absorbance. It is observed that as the sample probe is moved toward the sample, the intensity initially drops off rapidly, then a spike is observed, then the intensity can rise rapidly or continue to drop off. The spectra represent a complex interaction of the sample probe with the tissue. The initial drop in intensity at 1271 nm and regions thereabout, such as 1150 to 1350 nm, is due to the decreased collection of specularly reflected light as the sample probe moves toward the sample. The spike is due to at least one of several phenomenon. The spike is partly due to contact of the sampling probe with the fluorocarbon fluid on the sample. Pressure builds up as the probe moves into the fluid and excess fluid is pushed out of the sampling path. During this time and at subsequent times, the sampling probe applies pressure to the sample resulting in the stretch of collagen that results in an increase in the scattered light. Also, some water is displaced from the sample resulting in the relative concentration increase in scatterers and an increase in the scattered light. In addition, it is determined that the amount of scatter is related to the amount of collagen in the sampled path. Therefore, older women, for example, who have less collagen have less of a change in the observed scattered light in the second overtone region.

Figure 17:
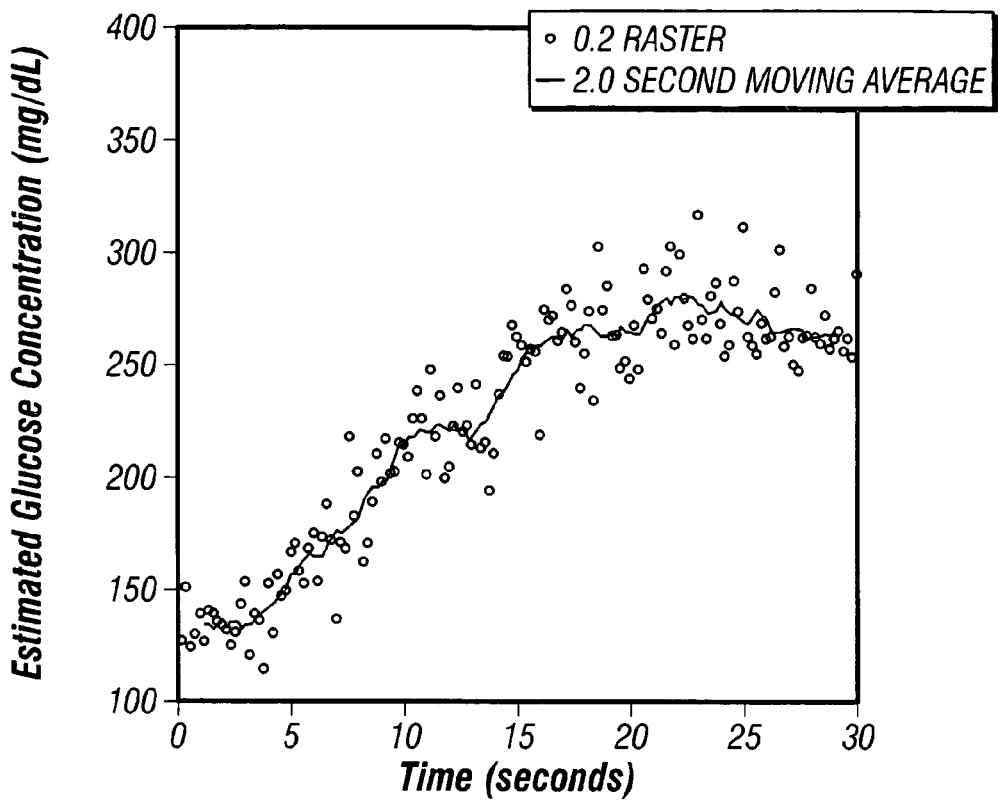
FIG. 17 presents estimated glucose concentrations for all rasters of varying z-axis positions of a sample probe relative to the sample for a given sample of a given subject according to the invention.

For every raster spectrum of the given sample of the given subject, a glucose concentration estimation is performed using the model generated with the calibration and monitoring data. The results are presented in FIG. 17. It is observed that a wide range of glucose concentration estimations result ranging from approximately 100 to 300 mg/dL. This is an indication of spectra that do not fall within the space covered by the calibration model. For example, the initial spectra where spectral reflectance is strong predict at low glucose concentrations. In addition, the precision of the glucose concentration estimation is poor for a given raster. The solid line indicates an average glucose concentration estimation from a moving window of two seconds of data collection, ten rasters at the 5 Hz collection rate. This greatly increases the precision of the glucose concentration estimation. In addition, as the sample probe reaches the sample, the glucose concentrations begin to level off. Then, with initial contact of the sample probe with the sample, relatively stable glucose concentration estimations result. Co-adding the later scans results in sufficient signal-to-noise ratios to allow clinically accurate and precise glucose concentration estimations. Therefore, it is important to select appropriate z-axis varying raster spectra for glucose concentration estimation. A common approach for making this selection is to select spectra with high absorbance where water absorbs, using a threshold for determining acceptable rasters. Alternatively, ratios of intensities of two wavelengths are used with a threshold. One such ratio uses a first wavelength of high absorbance where little response intensity is expected, and a second wavelength where high intensity is expected, such as about the middle of the first or second overtone region. Multiple approaches for selecting rasters are presented, infra.

A series of preprocessing steps is performed on the data of a given sample of a given subject that reduces the number of spectra. Typically, the data are reduced in number by selection of spectra and are processed to a reduced number of spectra with chemometric techniques, such as averaging and mean centering. In this example, a ratio of intensities is calculated for each raster scan using intensities at 1455 and 1255 nm. Subsequently, the log of the ratio is calculated for each z-axis position scan of a given sample. Samples corresponding to the top 20% of the sample in terms of this log ratio are selected and the resulting set of spectra is averaged. Subsequent preprocessing and processing is identical to preprocessing and processing of the calibration data set. The preprocessing and processing approach is generated with the calibration and monitoring data sets independent of any estimation data. The preprocessing approach has three steps:

Step 1: perform a 27-point first order derivative Savitsky-Golay convolution;

Step 2: selection of a data matrix associated with the 1150 to 1850 nm spectral range; and Step 3: mean centering.

Figure 18:
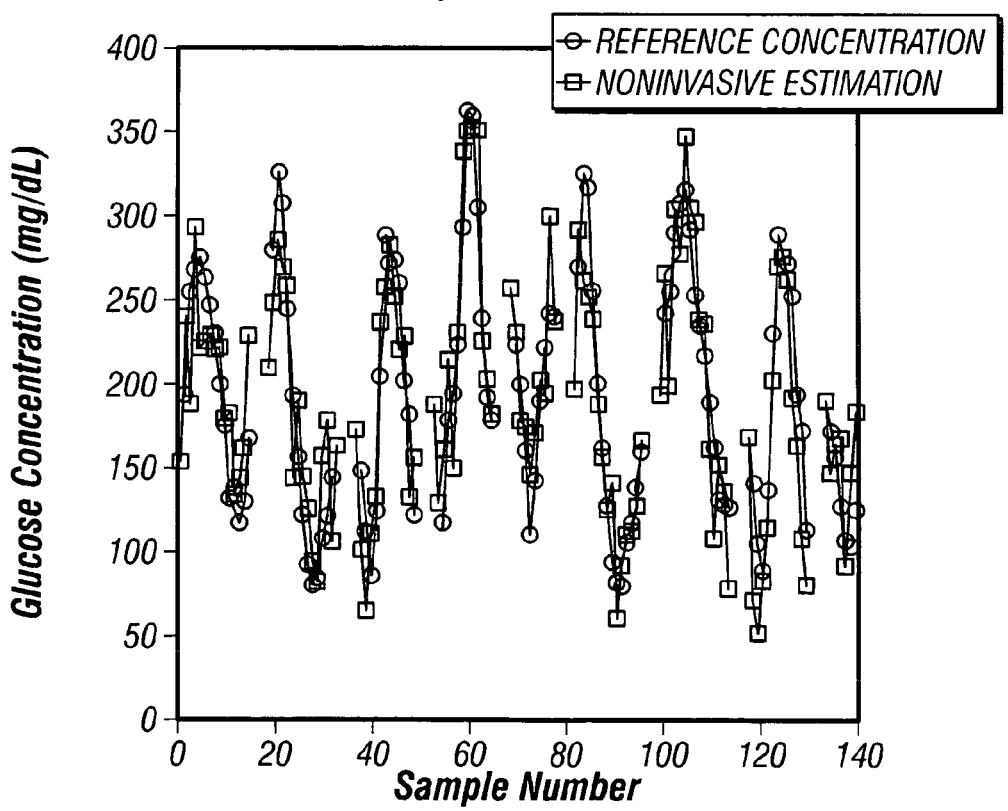
FIG. 18 presents reference and noninvasively estimated glucose concentration profiles for nine individuals according to the invention.

The resulting matrix is processed with a principal component regression (PCR) model using a total of 44 factors. The resulting standard error of estimation, which is also loosely referred to as a standard error of prediction (SEP), on the new samples is 32.2 mg/dL. Using this processing, the independent prediction data set is analyzed. The glucose concentration profiles for each of the nine test subjects used in the independent prediction set are presented in FIG. 18. The glucose concentration profiles are in the shapes of: up/down, down/up/down, and up/down/up to break correlations with variables changing with time, such as room temperature and humidity, and to break correlations with other body constituents. The calibration data are similarly varied. The resulting glucose concentration estimates for the nine individuals are overlaid onto the reference concentration profiles. It is observed that the noninvasive glucose concentration estimations track the reference glucose concentration profiles. The resulting glucose concentration estimations are presented in FIG. 19 in a concentration correlation plot versus the reference glucose concentrations. A Clarke error gird is overlaid onto this plot. A total of 69.8, 30.2, 0.0, 0.0, and 0.0% of the resulting glucose estimations fell into the A, B, C, D, and E regions of a Clarke error grid, respectively. Glucose concentration estimations in the A and B regions of the Clarke error grid are clinically accurate and precise. Therefore, 100% of the glucose concentration estimations are clinically acceptable. The resulting F-value is 4.37.

ALTERNATIVE EMBODIMENTS

Alternative Instrumentation

Motion Control Systems

An alternative embodiment of the invention is presented in FIGS. 20A and 20B. In the first embodiment, the drive motor is remote from the sample probe. However, placing the drive system in the sample module allows the system to be simpler. In this embodiment, means for driving the sample probe are in close proximity, are directly attached to the sample probe, or are indirectly attached to the sample probe. In the example pictured embodiment, the drive means 2001 is connected to the sample probe 2003 by movement means 2002, such as a lead screw. Operation of this embodiment is illustrated at Time 1 (FIG. 20A) and Time 2 (FIG. 20B).

Figure 21:
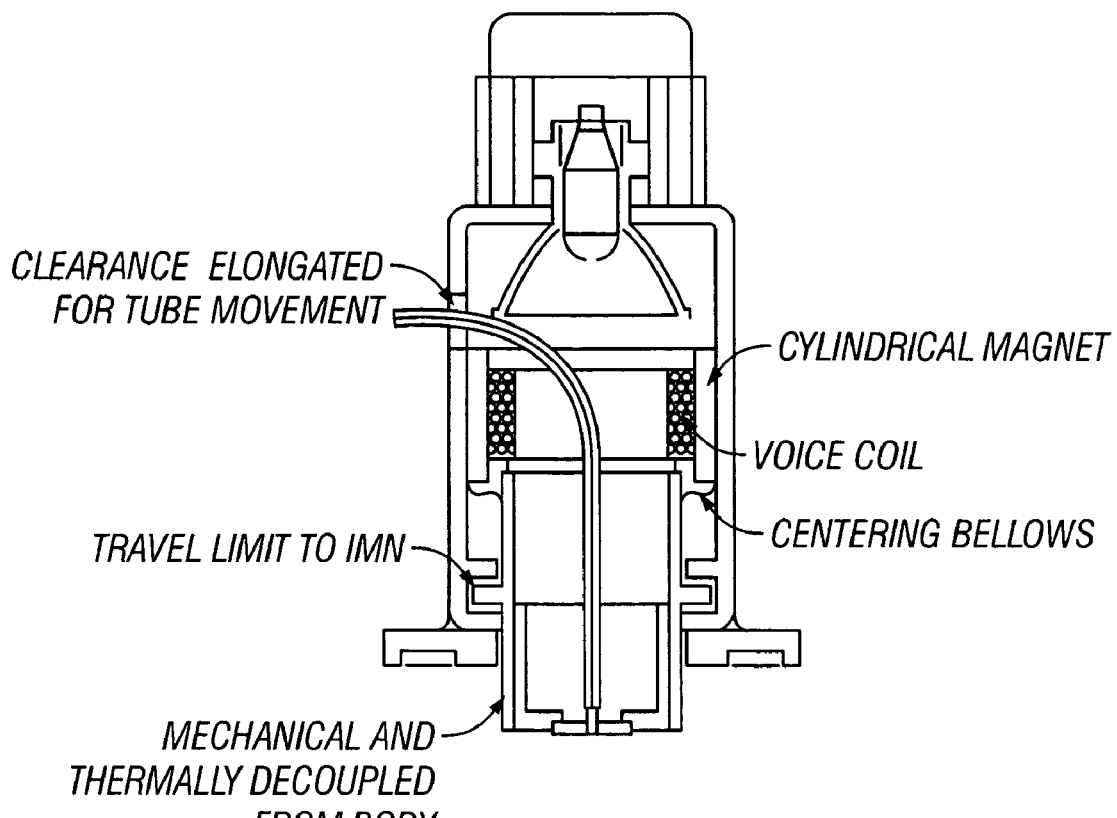
FIG. 21 presents an electromechanical embodiment of a dynamically controlled sample probe interface according to the invention.

In another embodiment of the invention, an electromagnet/permanent magnet pair is driven by a controller, see FIG. 21. The magnet pair moves the sampling probe along the z-axis relative to the tissue sample. In this embodiment, the tip of the collection fiber and the sample interface window are displaced to, and optionally into, the tissue sample. Alternatively, the source and associated optics such as a backreflector, optical filters, and sample probe tip are all moved by the actuator. Moving the sample module optics together reduces the impact of optical coupling and light distribution incident onto the tissue sample. In both embodiments (FIGS. 20A/20B and 21), the collection fiber, optionally, penetrates through the interface window and is flush with the surface of the sample interface window to reduce the impact of specular reflection off of the skin.

The movement of the sample probe elements is preferably over a limited distance, such as from about 0 to 10 mm. This magnet pair is capable of sample probe movements of less than 0.1 mm. Control of the positioning of the sample probe is optionally performed with an encoder, a mechanical stop, or mechano-electrical components. The movable half of the magnetic pair is either of the permanent magnet or the electromagnet. In the preferred version of this embodiment, the permanent magnet moves subject to the current in the electromagnet.

Figure 22:
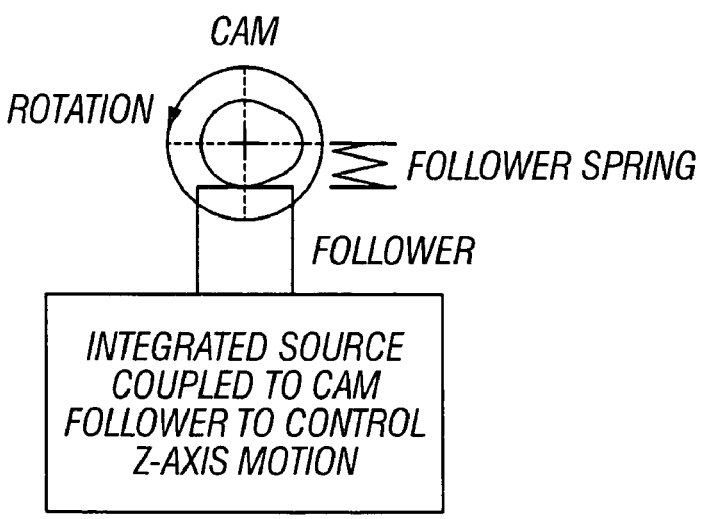
FIG. 22 presents a cam driven sample probe according to the invention.

In yet another embodiment of the invention, a cam is used to couple the drive to movement of the sample probe, see FIG. 22. For example, a cam with an eccentric lobe is used to convert rotational motion of drive means to linear sample probe movement.

Figure 23:
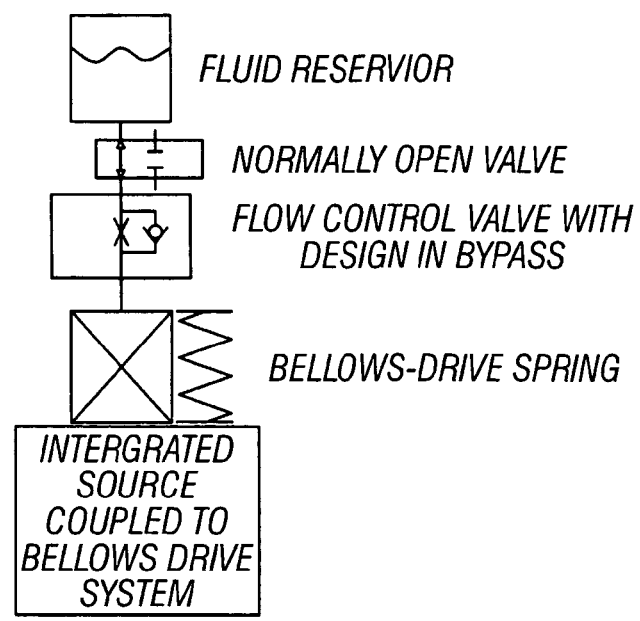
FIG. 23 presents a fluid regulated drive system for displacement of the sample probe according to the invention.

In still yet another embodiment of the invention, a fluid regulated drive system is used to move the sample probe along the z-axis relative to the tissue sample. Fluid pressures are used to move the sample probe, see FIG. 23. The fluid regulated drive system includes: a fluid reservoir, a valve or aperture control, and a bellows. The system can operate over a wide range of pressure. However, the system preferably operates at high pressure, such that the displacement of the sample probe is linear with time allowing tight control of the sample probe position. An advantage of the fluid regulated system is that it is, optionally, a passive system.

In yet another embodiment of the invention, the sample module rests on the sample site and at least part of the sample module, such as the sample probe, is pulled toward the sample site by gravity. The applied pressure to the sample site is mitigated by distributing the weight of the sample module over an area. Optionally, the sample probe tip uses detachable tips with different surface areas. This allows the weight of the probe tip to be distributed yielding different pressures on the sample site and different displacements of the tissue sample.

In an additional embodiment of the invention, the tip of the sampling probe is the tip of a fiber bundle that includes a single collection fiber, a spacer surrounding the collection fiber, and illumination fibers or an illumination ring about the spacer. In this example, the maximum optical depth into the sample is larger than the spacer cross section.

In another embodiment of the invention, dynamic z-axis movement is used in combination with movement along at least one of the x- and/or y-axes. In this embodiment, the freedom of movement of the sample probe is not restricted to the z-axis. The probe used one or more drive mechanism to control movement of the sample probe along any or all of the x-, y-, and z-axes so that the sample probe moves along a line, plane, or in three-dimensional space as a function of time. Directions are given to the analyzer (measuring system) with a targeting system or by using the analyzer signal to target a sample. Hence, the dynamic z-axis movement is directed to a given sample location. The use of a targeting system used in combination with the analyzer is further described in U.S. provisional patent application No. 60/656,727 filed Feb. 25, 2005, which is incorporated herein in its entirety by this reference thereto.

In yet still an additional embodiment, the movement of the sample probe relative to the sample is only nominally controlled along the z-axis allowing reasonably controlled but not tightly controlled control about a central axis perpendicular to the skin. This is referred to as relatively perpendicular, a wobble, or slop in movement about the central perpendicular axis. This type of motion is either designed or is a result of inability to achieve perfect manufacturing tolerances.

There exist a large number of additional embodiments of the invention for moving a sample probe along a z-axis toward a sample site. These include:

- a permanent magnet/electromagnet pair;
- a hand crank;
- a motor gear combination;
- a lever arm;
- a scissors jack;
- a worm drive;
- a counter weight;
- a spring controlled system;
- air-pressure;
- a fluid regulated system;
- a hydraulic system;
- a bellows;
- a lead screw;
- a linear motor;
- a motor;
- a cam;
- a gravity controlled system;
- a controlled potential energy release;
- a rotating helix;
- a wedge;
- a rotating gear;
- a rotating piston;
- an electromechanical system;
- a memory metal;
- a magneto rheo-logical system;
- a controlled viscosity system;
- a magnetic system;
- a cable drive;
- a bladder;
- a pneumatic piston; and
- an expansion and contraction of a material, such as wax.

Other systems will be apparent to those skilled in the art. The intermediate means include mechanical, electromechanical, and hydraulic systems, as well as systems logically connected to the means for moving a probe.

In the above embodiments, the sample probe is part of the sample module. Alternatively, the sample probe is part of an analyzer that is not split into a base module, a sample module, and a communication bundle. In this embodiment, the sample probe is part of the analyzer and the sample probe moves along any axis toward a sample. For example, the analyzer sits on a desktop and the sample is positioned on the analyzer. The sample probe them moves up along a z-axis toward contact and displacement of the sample.

Feedback Control

In an additional embodiment, a z-axis movement profile is predetermined. Thus, the system is operating in an open-loop mode without feedback control of the z-axis movement of the sampling probe. In an alternative embodiment of the invention, the movement of the sampling probe relative to the sample is controlled by an algorithm in a closed-loop mode. In this embodiment, the algorithm uses input to control the z-axis movement of the probe. The input optionally includes spectral and/or thermal input or the output of an auxiliary sensor. For example, chemical and physical features observed in a spectrum of an auxiliary reference or the sample are used to control the movement of the sample module. One example is use of regions containing high water absorbance to determine via specular reflectance when the sample probe is adequately close to or in contact with the sample. Another example uses a ratio of spectral features to determine when appropriate optical contact is made. For example, a region of high and low absorbance is ratioed and the ratio is used against an a-priori threshold to indicate to the analyzer to stop the movement of the sampling module. In its broadest sense, absorbance, intensity, or scattering features of a reference or sample determined at one or more wavelengths provide an input to the algorithm that controls the movement of the sampling module relative to the sample. Alternatively, an input source outside of the collected spectrum is used as an input to the algorithm. Several examples include a pressure sensor on the skin, breaking the plain of a laser or optical signal across the sample site, and completing a contact electrically, magnetically, or electro-mechanically.

While embodiments are herein described separately, permutations and combinations of elements, embodiments, and systems described herein are also usable for dynamic positioning of the sample sensor and/or data acquisition by the analyzer with movement of the sample optical sensor tip with respect to a skin tissue sample site. For example, a closed loop system is applicable to many of the open-loop designs. In addition, each of the instrument designs herein is used with one or more of the algorithm approaches presented below.

Alternative Probe Movement

Preferably, the sample probe is moved, nominally, along the z-axis toward the sample between and/or during sample acquisition. Alternatively, the sample probe is moved toward or away from the sample site with different or varying velocity. In general, the movement of the sample probe is preferably controlled and/or reproducible. A known position relative to the skin is desirable, but this is not necessary. Also, it is preferable to know the z-axis velocity as a function of time, but is not necessary. It is generally preferable to move the sample probe into close proximity to the sample or to touch the sample surface. Generally, it is less desirable to displace the sample with the sample probe. However, displacement of the sample with the sample probe is sometimes preferable. For example, displacement of the sample tissue with the sample probe followed by withdrawing the probe results in fluid flow into the sample site. This increases the volume of the sample containing analytical information and aids in equalization of glucose concentration between body fluid compartments.

Figure 24:
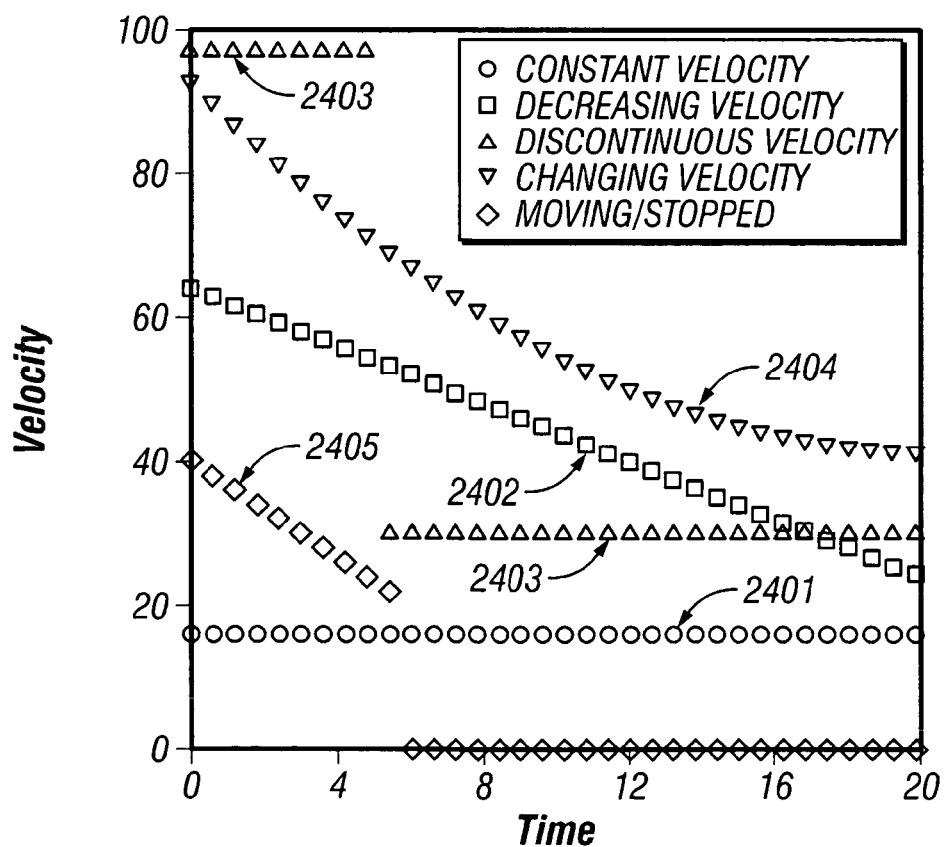
FIG. 24 presents velocity profiles of a sampling probe according to the invention.

A range of constant velocity movement rates of the sample probe toward or away from the sample are possible. A first example is a sample probe that moves at a constant velocity. Typical velocities range from about 15 to 100 μm/second. However, slower and faster velocities are used, such as about 5 to 200 μm/second. Two preferable movement rates are about 16 and 32.5 μm/second. Still slower velocities are used while initiating or stopping movement or when profiles are used that incorporate time intervals where a static probe movement is used. The actual movement rates are dependent upon other parameters, such as a cross sectional area of the hydraulic fluid delivery line. An example of a fixed velocity movement rate 2401 of the sample probe as a function of time is presented in FIG. 24.

The movement rate of the sample probe need not be at a fixed velocity. Several exemplary sample probe profile examples are provided in FIG. 24. One example, is a probe tip having decreasing velocity or a probe that is decelerating, such as that presented 2402. A decelerating probe velocity has an initial speed and a slope. The initial speed and slopes result in probe movements in a range of about those of the constant velocity probes at any given point in time. A second example is a discontinuous velocity profile, such as that presented 2403. A discontinuous velocity profile is any movement profile with a discontinuity or a period of rapid change in velocity. One instance where a discontinuous profile is used rapidly moves the sample probe to close contact with the sample. Proximity is determined visually or with an algorithm, such as an algorithm examining spectral contact or examination of a pedestal effect. A pedestal effect is specular reflectance and is described in U.S. Pat. No. 6,040,578, previously incorporated by reference. The pictured velocity profile 2403 is slower as the sample probe nears the sample. However, an increasing velocity is possible. A third example is a profile of changing velocity with time, such as pictured 2404. The changing velocity profile 2404 is designed to slow the movement of the probe toward the sample as the sample probe and sample proximity is decreased. A fourth example of a velocity profile is having the sample probe movement stop for a period before and/or during sample spectra acquisition 2505. Additional profiles of velocity of the probe as a function of time include sinusoidal, logarithmic, quadratic, or higher order polynomials. Still additional probe velocity profiles include symmetric and asymmetric profiles. Still additional probe velocity profiles are permutations and/or combinations of the above described profiles. For example, a probe that moves cyclically toward the sample and away from the sample where the cyclical pattern occurs one or more times and initiates and terminates at any point within a cycle. In the provided examples, it is the probe tip, sampling tip, or sampling module that is moved. Alternatively, the sample site is moved, such that the relative sample probe/sample site z-axis movement profiles described herein are obtained by moving the sample. These movements are preferably along the z-axis. However, movement along the x and/or y axes are used to change sampling location.

In the example provided, supra, the total z-axis movement of the sample probe toward the sample is 0.95 mm. The particular sample probe apparatus described in the above example has a movable throw distance of 1.3 mm. However, larger distances are readily achieved. For example, potential z-axis movement includes movements of sub-millimeter or about 1, 2, 3, 4, or 5 or more millimeters.

Generally it is advantageous to move the sample probe initially toward the sample. However, it is possible to place the sample probe initially in contact with the sample at either a minimal pressure or to displace part of a flexible sample with the sample probe at initial contact. At a later time, optionally after further displacement into the tissue, the sample probe is moved away from the sample. This creates a negative pressure as the skin sample relaxes. Typically, the scattering decreases with the relaxation. For example, the scattering coefficient decreases in the second overtone spectral region at or about 1290±100 nm.

Generally rasters or spectra are collected while the sample probe is moving and/or when it is stopped. In a first case, raster scans are collected while the sample probe is moving. In a second case, rasters are collected at a subset of the time period that the sample probe is moving. The subset of time is either continuous or is broken into two or more periods. The data or rasters are either collected and saved, or the data are compressed either in real time or on the fly. In a third case, rasters are collected at one rate during a first time period and at a second rate during a second time period. For example, rasters are collected less frequently as the probe is approaching the sample and when correct placement of the probe is achieved rasters are collected rapidly. An advantage of collecting during a subset of the movement time is a smaller requirement for storing rasters. In a further memory saving mode, once an algorithm determines acceptable rasters are being collected, the rasters are averaged or a mathematical transformation is calculated, such that only a subset of the space requirement for saving all rasters is required. An example is a running average. A second example is compression of the data.

In yet another embodiment of the invention, the sample probe is first moved while collecting all rasters, while an intermediate number of raster are collected, or with collection of no rasters. The movement of the sample probe is then stopped. A second set of rasters are collected while the sample probe is stopped. An example of this configuration is moving the sample probe until an algorithm establishes appropriate contact with of the sample probe with the sample. The algorithm, optionally, uses a first set of rasters to determine when to stop movement of the sample probe. The sample probe is then stopped and a second set of rasters is collected. The second set of rasters is processed as the primary data set of rasters as taught herein. An alternative to a closed loop algorithm determined stop-point is an open loop system where the sample probe is moved over a predetermined profile before stopping. Variations, such as move/stop/read and repeat move/stop/read, are also used.

In still an additional embodiment of the invention, the sample probe is moved through a repeated profile, such as a sinusoidal wave pattern. The resultant rasters are collected at various degrees of no contact, contact, and/or displacement. A lock-in algorithm is then used to filter out unwanted signals as a function of displacement.

Alternative Algorithms

In general, the rasters of each sample provide spectral information and z-axis information. The rasters are processed with a variety of chemometric means to generate one or more resulting single beam intensity spectra. The resulting single beam spectra are processes using chemometrics to yield one or more subsequent analyte concentrations. Examples of preprocessing and processing means are provided in U.S. provisional patent application Ser. No. 60/558,610 (attorney docket number SENS0007PR) and U.S. provisional patent application Ser. No. 60/599,431 filed Aug. 6, 2004 (attorney docket number SENS00053PR) which are herein incorporated in their entirety by this reference thereto.

Information contained in the dynamic spectral transient is used to select a range of spectral scans, or a sampling of spectral scans over a period of time, that best represent optical properties having a relationship between the spectral response and the chemical composition. This selection of spectra preferably represents a reproducible optical sample that simplifies the quantitative optical spectral measurement. Alternatively, this selection of spectra is performed through an intelligent system that selects spectra within a given calibration cluster. Calibration clusters are further described in U.S. patent application Ser. No. 09/664,973 (filed Sep. 18, 2000), which is herein incorporated in its entirety by reference, and in T. Blank, S. Monfre, T. Ruchti, and S. Thennadil, A multi-tier method of developing localized calibration models for non-invasive blood analyte prediction, U.S. Pat. No. 6,512,937 (Jan. 28, 2003), which is herein incorporated in its entirety by reference. In either case, the selection of one or more time windows permits measurement over a wide range of sample probe displacements of the tissue sample including small displacements that correlate with small applied pressures. This selection is important in many cases including the case where the optimal measurement pressure is related to a given subject's skin properties and in cases where daily or weekly skin hydration changes lead to changes in contact pressure at specific displacements of tissue sample by the sample probe.

The collection of a continuum of spectra during the movement of the optical probe provides enhanced information that is beneficial to the accuracy of noninvasive glucose concentration estimation. The form of this data is twofold. First, a time series of spectra is collected that is sampled uniformly or discretely through time. Second, a time series of data is sampled relative to the penetration of the probe into the tissue. Both sets of time series data provide unique information including the characterization of the tissue type, the selection of the optimal preprocessing methods, the detection of erroneous measurements, and the determination of the most suitable calibration model. In addition, the time series spectra form a matrix or cube that is very similar to an image. This two dimensional information is linked to the tissue type and to the dynamics of the optical probe. This provides an opportunity to further resolve the net analyte signal through a multi-way data analysis. The various uses of the multi-dimensional data are categorized into wavelength versus time, wavelength versus position, and an image formed by wavelength versus both time and position.

The nature of spectral variation with time and displacement allows classification of the tissue type and the nature of an interference. This, in turn, allows the selection of the most suitable calibration model for making a noninvasive estimation of an analyte property. Previously, tissue types are categorized according to the nature of the spectral variation observed in time series measurements. The categorized data are used to generate calibration models associated with each cluster. Finally, calibrations are selected based on the tissue types revealed by the time series measurements and applied for noninvasive analyte estimation or determination. For example, the multivariate time series spectra are used with a Kalman or extended Kalman filter to determine the state of the tissue. Alternately, a key set of spectral features, such as the time related variation response of water, fat and protein bands are used to identify the tissue type and state. Finally, the variation of scores determined from an abstract factor analysis is used to model and characterize various tissue properties and enable a determination of tissue type.

The two-dimensional time or displacement data and the three-dimensional time and displacement data sets provide greater power to discriminate the net analyte signal related to the analytical signal through image processing techniques and multiway analysis. The higher order measurements are linked by the contact dynamics of the probe and the nature of the tissue. This link enables use of higher order methods for the detection and extraction of the net analyte signal related to the analyte. For example, the following multiway methods are used in conjunction with the floating probe system and time series spectral information: rank annihilation factor analysis, generalized rank annihilation method, parallel factor analysis, and multiway calibration.

The inventors have determined that selection of the rasters to be used for subsequent data analysis is important. In some cases, all of the rasters are selected. For example, the rasters are averaged to increase the signal-to noise-ratio. In another case, time-series analysis is performed to determine outliers, and/or differences in the rasters in order to select rasters for subsequent analyses. In still an additional case, outlier detection is performed to select rasters meeting specifications. For example, individual rasters are examined based upon a metric, such as a signal-to-noise ratio or sample probe/tissue sample contact distance. Rasters passing the metric are combined into a data set that is subsequently processed. Examples of a metric include signal to noise ratios, one or more intensity thresholds, and/or one or more absorbance thresholds. In yet another example, one or more bands of rasters are used in subsequent analysis. For instance, only rasters with a sufficient signal-to-noise ratio are selected, rasters are selected where coupling to the sample is indicated, or rasters are selected where contact with the sample is indicated. Spectra associated with selected rasters are then used in subsequent analysis. Some examples of preprocessing the rasters are provided here.

The inventors have determined that selection of rasters, and their associated spectra, after contact of the sample probe with the sample is beneficial. A spike in the raster profile versus time or position is associated with contact. Therefore, multiple techniques are developed for determining contact using the spike. Additional techniques are used for determining contact that don't use the spike. Several examples follow.

Figure 25:
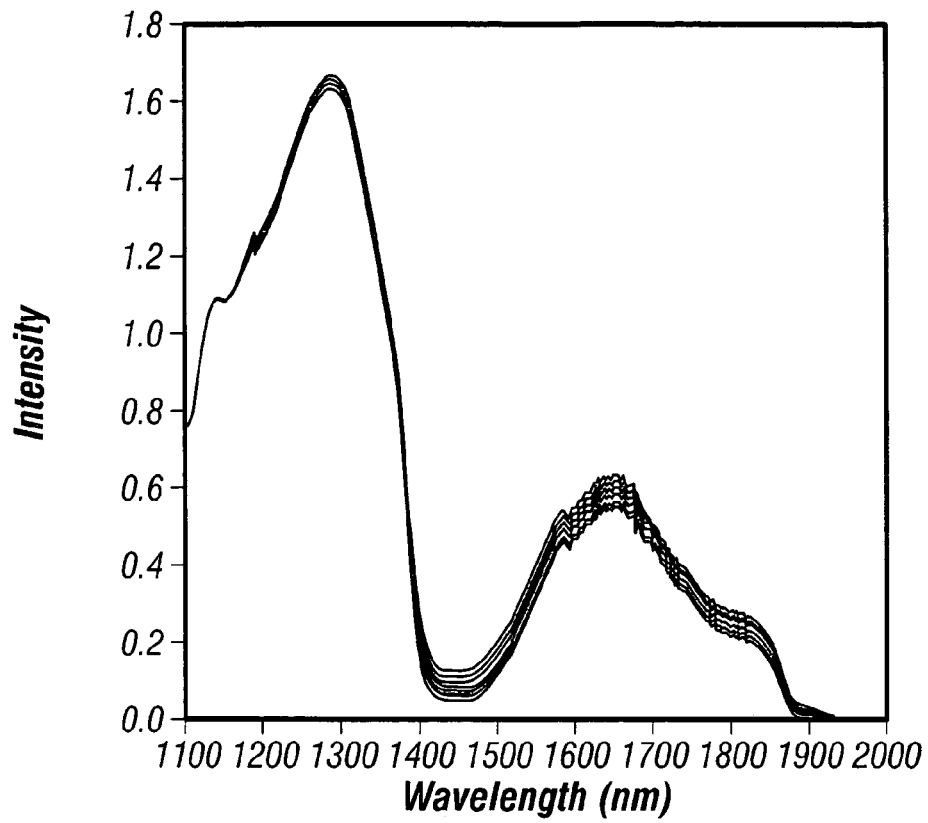
FIG. 25 presents raster intensity spectra at varying sample probe to sample distances according to the invention.

Referring now to FIG. 25, multiple intensity rasters, collected for a single sample on a single subject, are presented. One approach to determining contact is to select spectra where one or more intensities at pre-selected wavelengths, or optionally absorbances at pre-selected wavelengths, fall above or below a threshold, a ratio, or a metric. For example, rasters having an intensity below a threshold at 1450 nm are kept. The threshold is general, customized for a type of subject, or is specific to a subject. At 1450 nm, exemplary thresholds are about 0.05, 0.1, 0.15, or 0.2 volts. Similar threshold techniques are used at other wavelengths with, optionally, different thresholds. Thresholds are also developed using signal from multiple wavelengths, combinations of wavelength, ratios, clustering analysis, or from mathematical transformations of the data. If the metric is met for the tested wavelength or wavelengths, then the spectrum associated with the raster is used in subsequent analysis.

Figure 26:
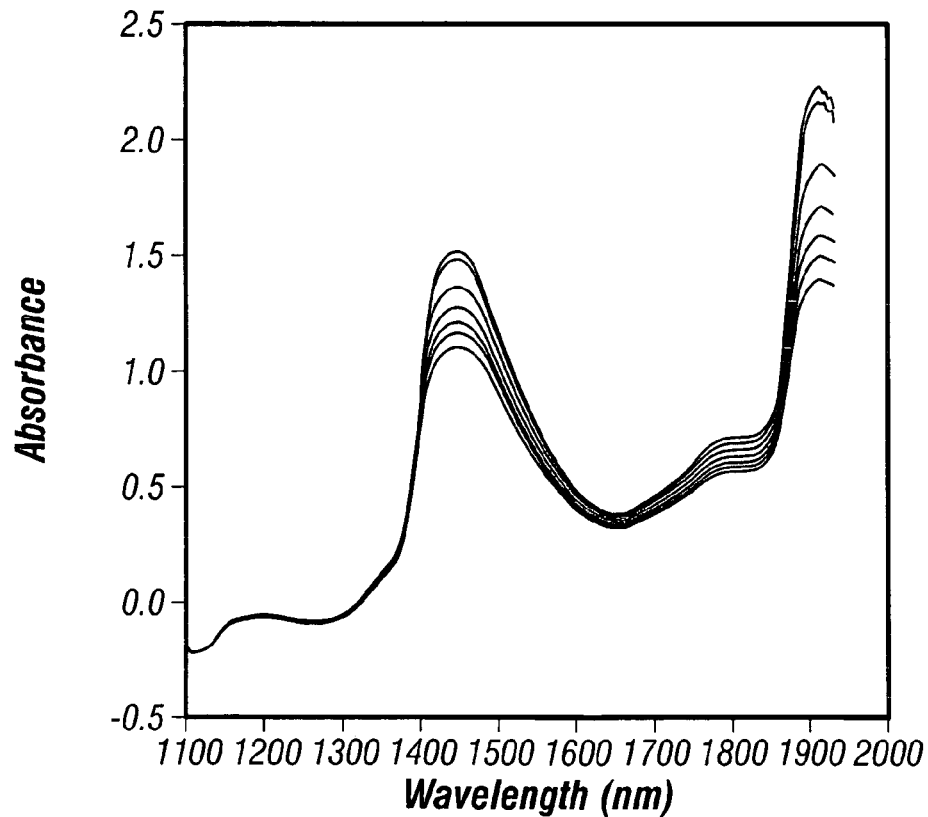
FIG. 26 presents raster absorbance spectra at varying sample probe to sample distances according to the invention.

Another approach is to select windows or blocks of rasters, and their corresponding spectra, using one or more selection criteria. For example, rasters are collected based upon a time cutoff, based upon a time period, based upon position of the sampling probe, based upon a spectral feature, or based upon changes in signal as a function of time or position. The intensity rasters collected for a single sample on a single subject presented in FIG. 25 are analyzed here, by way of example, using a combination of these approaches. As the sample probe is moved along the z-axis toward the sample, the intensity about the water bands centered at 1450 and 1950 nm are observed to decrease. This is a result of changed efficiency of optical coupling with relative distance between the sampling probe and the sample. The intensity spectra are converted to absorbance and are presented in FIG. 26, which demonstrates that at wavelengths longer than 1400 nm, a change in absorbance is observed with movement of the z-axis probe. These longer wavelengths are dominated by absorbance. At shorter wavelengths, changes in absorbance exist, but they are not as strong. From 1100 to 1400 nm, scattering has a larger effect than from 1400 to 1930 nm. The raster intensities at 1450 nm and 1290 nm are representative of intensities where absorbance dominates and where scattering has a relatively large effect, respectively.

Figure 27:
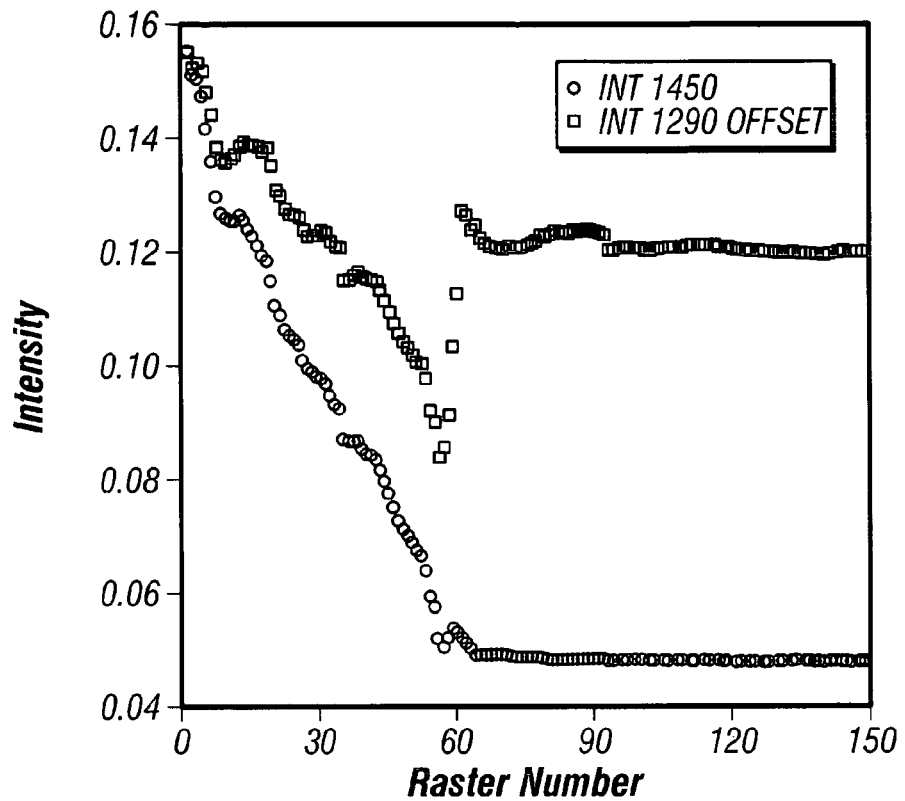
FIG. 27 presents raster intensities at 1450 and 1290 nm for a single replicate according to the invention.

Intensity, or absorbance, profiles of rasters at individual wavelengths are used to determine time points, such as contact of the sample probe with the sample. For example, the raster intensities collected at 1450 and 1290 nm are plotted as a function of raster number in FIG. 27. The intensity at 1450 nm is observed to decrease and then level off. The change in slope is an indication of contact of the sampling probe with the sample. This elbow shape is used to set a time point. Typically rasters after this time point are used in subsequent analysis. However, rasters before or before and after this time point are optionally used in subsequent analysis. The elbow point is an effective method of establishing contact. However, improvement of the sensitivity is possible. For example, the intensity at 1290 nm for each raster of the given sample is also plotted in FIG. 27. The intensity is offset for presentation. The intensity is observed to decrease initially and then to spike upward. Generally, intensities in the region from 1100 to 1300 nm decrease until contact of the sample is made by the sampling probe. After contact, the intensities from 1100 to 1330 generally increase. Therefore, the change in direction of the intensity profile is indicative of contact and is used to set a time point.

Figure 28:
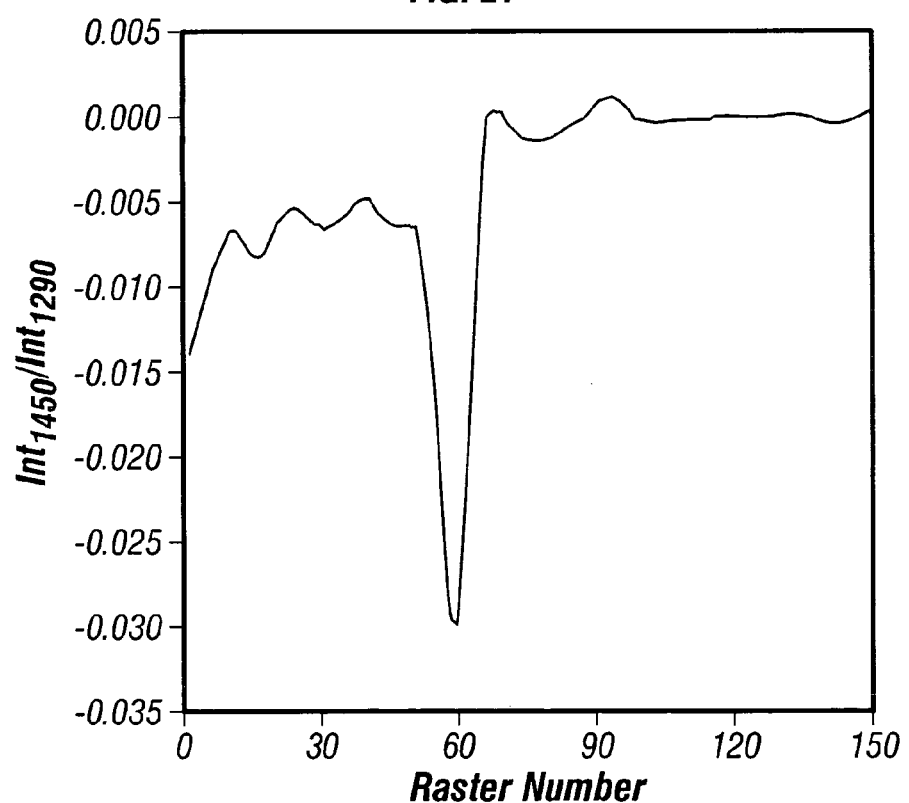
FIG. 28 presents a derivative of a ratio of raster intensities according to the invention.

Alternatively, combinations of responses of raster intensities are used to determine which spectra associated with selected rasters are to be used in subsequent analyses. For example, a ratio of raster intensities is used. An example is ratios of each of raster intensity at 1450 nm to the offset raster intensity at 1290 nm. Plotting the ratio versus time yields a clear breakpoint associated with the sampling probe making contact with the sample. An 11-point Savitsky-Golay first derivative is applied to the ratio of the 1450 to 1290 nm ratio and is presented in FIG. 28 as a function of time. The large negative peak indicates contact. This is sensitive and robust technique for determining the raster that is associated with the sampling probe making contact with the sample. Optionally, this time period is used as an internal standard allowing selection of time periods that are consistent in terms of raster number between samples or between individuals. In this example, spectra associated with z-axis movement after the large negative derivative peak are used in subsequent analysis.

In another embodiment of the invention, time series analysis of the rasters is used to determine when adequate tissue contact is made with the techniques described above in terms of scattering and absorbance signals, such as the water, fat, and protein bands.

In yet another embodiment of the invention, differential measurements are made using the spectra or parts of the spectra associated with different z-axis positions or time periods. Different spectral responses are generated as the sample probe moves toward the sample, into the sample, out of the sample, or away from the sample. Differential techniques are thus applicable to the spectra collected at different z-axis position or time periods. For example, upon initial contact the sample is not compressed. After displacing the sample probe further into the sample some of the layers of skin become compressed. This compression alters the physical sample, such that analytical signals are changed. For instance, the capillary regions are compressed and the glucose signal decreases as the analyte is displaced from the sampled tissue volume. Similarly, differential measurements are made using different rasters from the same sample. This mode of analysis is usable with a single or with multiple displacements of the tissue sample by the sample probe In still yet another embodiment, pattern recognition is employed to determine the optimal time slice of vectors for noninvasive analyte measurement. An a-priori basis set is employed exemplifying target tissue states. The measured times series of spectra are compared to this basis set to determine the optimal data for measurement.

In another embodiment of the invention, outlier determinations are performed on the rasters. The nature of the spectral variation over time enables the determination of invalid measurements. For example, grossly changing spectra features are consistent with poor surface contact or substantial tissue distortion. Key features that represent surface contact and tissue distortion are compared with previously accepted limits to identify invalid spectra as described, supra.

In these examples, intensity is used. It is also recognized that mathematical transformations of the spectra are also useable. For example, analysis of pseudo-absorbance or absorbance spectra is performed with equivalent techniques.

In these examples, particular wavelengths are used. It is recognized that a large number of wavelengths in the near-infrared carry equivalent information. Many of the wavelengths over the entire collected spectral region are applicable for many of the techniques taught herein.

Combinations of analytical techniques are also used to select and analyze data. In its broadest sense, one or more chemometric technique is used to select and process spectra or parts of spectra associated with one or more z-axis positions of the sampling module relative to the sample.

In the foregoing discussion, the preferred embodiments of the invention have been described with respect to estimation of a glucose concentration. Additional analytes for concentration or threshold determination are those found in the body including: water, protein, fat and/or lipids, cholesterol in its various forms, blood urea nitrogen (BUN), both therapeutic and illicit drugs, and alcohol.

Those skilled in the art will recognize that the present invention may be manifested in a variety of forms other than the specific embodiments described and contemplated herein. Departures in form and detail may be made without departing from the spirit and scope of the present invention. Accordingly, the invention should only be limited by the claims included below.

The invention claimed is:

1. A method for noninvasive estimation of a tissue sample property, comprising the steps of:
providing an analyzer, wherein said analyzer comprises:
a sample probe coupled to said analyzer, said sample probe being movable with respect to said analyzer, and said sample probe having a tip;
displacing at least a portion of said tissue sample with said sample probe;
collecting a set of time serial spectral data of said tissue sample at least during said step of displacing;
selecting a sub-set of said set of spectra, wherein sampling precision is enhanced; and
estimating said tissue sample property using said sub-set.

2. The method of claim 1, wherein movement velocity of said sample probe tip ranges between about zero and about one hundred micrometers per second.

3. The method of claim 1, wherein said step of displacing moves only a portion of said sample probe.

4. The method of claim 1, wherein said step of selecting further comprises any of the steps of:
removing at least one outlier spectrum; and
calculating a ratio of response from at least one wavelength of high absorbance and at least one wavelength of low absorbance.

5. The method of claim 1, wherein said step of selecting further comprises the step of:
extracting a feature from said set of spectra.

6. The method of claim 5, further comprising the step of:
providing an algorithm, said algorithm integrated with said analyzer, wherein said algorithm uses said feature iteratively to control at least one of:
said step of displacing; and
said step of collecting.

7. The method of claim 1, further comprising the step of:
providing an algorithm, said algorithm integrated with said analyzer, and said algorithm used to control at least one of:
said step of displacing; and
said step of collecting.

8. A method for determining a blood/tissue analyte concentration, comprising the steps of:
providing a noninvasive analyzer, comprising:
a sample probe, wherein at least part of said sample probe is movable relative to said analyzer;
iteratively collecting a positioning spectrum at a first rate;
using at least a portion of said positioning spectrum to establish contact of said sample probe with said tissue;
collecting a set of spectra at a second rate; and
using at feast a portion of said set of spectra to estimate said analyte property.

9. The method of claim 8, wherein said second rate is faster than said first rate.

10. The method of claim 9, further comprising the steps of extracting a feature from said set of spectra;
removing any outlier spectrum based upon said feature;
preprocessing said sub-set of spectra to create a set of preprocessed spectra; and
applying multivariate analysis to said set of preprocessed spectra in conjunction with said step of estimating.

11. An apparatus for spectroscopic noninvasive measurement of a tissue sample, comprising:
a noninvasive analyzer;
a sample probe coupled to said analyzer;
means for moving at least part of said sample probe along any of x-, y-, and z-axes
means for acquisition of at least one spectrum while said sample probe is moving; and
at least one algorithm for analysis of said spectrum, wherein said at least one algorithm provides for iterative control of said means for moving and said means for acquisition of said spectrum.

12. The apparatus of claim 11, wherein said algorithm comprises a preset movement profile of said sample probe.

13. The apparatus of claim 11, wherein said algorithm adjusts movement of said sample probe based upon any of:
chemical information derived from said spectrum;
physical information derived from said spectrum;

a feature extracted from said spectrum;
an intelligent system;
a pattern recognition system; and
an auxiliary sensor reading.

14. The apparatus of claim 13, wherein said physical information comprises any of:
specular reflectance; and
scattering information.

15. The apparatus of claim 13, wherein said auxiliary sensor reading comprises any of:
pressure;
temperature;
an electrical reading; and
a detector output.

16. The apparatus of claim 11, wherein said means for moving reside at least in part outside of said sample module, to reduce weight of said sample module.

17. The apparatus of claim 11, wherein said sample probe comprises:
a positively curved sample probe tip.

18. The apparatus of claim 11, wherein said iterative control is based upon a metric derived from said spectrum.

19. The apparatus of claim 18, wherein said metric derives from any of:
a region of high absorbance;
a region from 1100 to 1400 nm; and
a ratio of response from said region of high absorbance and said region from 1100 to 1400 nm.

20. The apparatus of claim 11, wherein said sample module weighs less than about 100 grams.

21. The apparatus of claim 11, wherein said sample module further comprises
means for distributing weight of said sample module about said tissue sample.

22. The apparatus of claim 21, wherein said means for distributing weight comprise any of:
one or more posts;
a set of feet;
a fluid filled membrane; and
a deformable membrane, wherein said deformable membrane adapts to a tissue sample shape.

23. A method for analyte property estimation of a tissue sample, comprising the steps of:
providing an analyzer, comprising:
a sample probe having a sample probe tip;
dispensing a coupling fluid on said tissue sample;
iteratively controlling z-axis movement of said sample probe tip relative to said tissue sample to contact said sample probe tip with said coupling fluid;
collecting at least one noninvasive spectrum of said tissue sample using said sample probe and said analyzer;
using said spectrum as feedback in said step of iteratively controlling movement; and
estimating said analyte property using said noninvasive spectrum.

24. The method of claim 23, further comprising the steps of:
extracting a feature from said spectrum; and
using said feature in a feedback loop for said step of iteratively controlling movement of said sample probe tip.

25. The method of claim 23, wherein said step of iteratively controlling said movement results in no direct contact between said sample probe tip and said tissue sample.

26. An apparatus for spectroscopic noninvasive measurement of a tissue sample, comprising:
a noninvasive analyzer;
a sample probe coupled to said analyzer;
means for moving at least part of said sample probe along at least one of x-, y-, and z-axes;
means for acquisition of at least one spectrum while said sample probe is moving; and
an algorithm for analysis of said spectrum, wherein said algorithm provides iterative control of said means for moving and said means for acquisition of said spectrum.

* * * * *